United States Patent
Kriheli

(10) Patent No.: US 11,730,679 B2
(45) Date of Patent: Aug. 22, 2023

(54) COMPONENTS OF A FLUID TRANSFER APPARATUS

(71) Applicant: EQUASHIELD MEDICAL LTD., Tefen Industrial Park (IL)

(72) Inventor: Marino Kriheli, Tel Aviv (IL)

(73) Assignee: EQUASHIELD MEDICAL LTD.

( * ) Notice: Subject to any disclaimer, the term of this patent is extended or adjusted under 35 U.S.C. 154(b) by 221 days.

(21) Appl. No.: 17/104,574

(22) Filed: Nov. 25, 2020

(65) Prior Publication Data

US 2021/0077354 A1 Mar. 18, 2021

Related U.S. Application Data

(62) Division of application No. 15/579,615, filed as application No. PCT/IL2016/050590 on Jun. 6, 2016, now Pat. No. 10,881,583.

(30) Foreign Application Priority Data

Jun. 11, 2015 (IL) ............................... 239366

(51) Int. Cl.
  *A61J 1/20* (2006.01)
  *A61M 5/31* (2006.01)
  (Continued)

(52) U.S. Cl.
  CPC .............. *A61J 1/2096* (2013.01); *A61J 1/00* (2013.01); *A61J 1/10* (2013.01); *A61J 1/1406* (2013.01);
  (Continued)

(58) Field of Classification Search
  CPC ...... A61J 1/2096; A61J 1/2072; A61J 1/2017; A61J 1/10; A61J 1/201; A61J 3/002;
  (Continued)

(56) References Cited

U.S. PATENT DOCUMENTS 3,543,967 A  12/1970 O'Connor
4,030,498 A  6/1977 Tompkins
(Continued)

FOREIGN PATENT DOCUMENTS

CN  1665562 A  9/2005
CN  202207309 U  5/2012
(Continued)

OTHER PUBLICATIONS

Japanese Search report for Japanese patent application 2020-196100, dated Nov. 8, 2021 (17 pages).

*Primary Examiner* — Erich G Herbermann
*Assistant Examiner* — Alessandro R Del Priore
(74) *Attorney, Agent, or Firm* — Whitestone Law, PLLC

(57) ABSTRACT

A system having a syringe and a connector. A proximal end of an outer housing of the connector is a specially designed female Luer element. A distal end of an outer housing of the connector is configured to connect the syringe to a component of a fluid transfer apparatus. The syringe and the connector are configured to be joined together such that they can be swiveled relative to each other around their common longitudinal axis. Once connected together, any attempt to twist the syringe or connector relative to each other in either a counterclockwise direction or a clockwise direction will result in endless swiveling about their common longitudinal axis. In other words, once the system is connected together, the syringe cannot be disconnected from the connector.

2 Claims, 18 Drawing Sheets

(51) Int. Cl.
*A61J 1/00* (2023.01)
*A61J 1/14* (2023.01)
*A61M 5/14* (2006.01)
*A61M 39/10* (2006.01)
*A61J 1/10* (2006.01)

(52) U.S. Cl.
CPC ............. *A61J 1/201* (2015.05); *A61J 1/2055* (2015.05); *A61J 1/2065* (2015.05); *A61M 5/1413* (2013.01); *A61M 5/31* (2013.01); *A61M 39/10* (2013.01); *A61M 2039/1077* (2013.01)

(58) Field of Classification Search
CPC ...... A61J 1/2055; A61J 1/1475; A61J 1/2013; A61J 1/145; A61J 1/209; A61J 1/00; A61J 1/2065; A61J 1/1406; B65D 51/002; A61M 5/162; A61M 2005/1623; A61M 39/24; A61M 39/10; A61M 5/31; A61M 5/1413; A61M 2039/1077; Y10T 29/49826
See application file for complete search history.

(56) References Cited

U.S. PATENT DOCUMENTS

| | | | |
|---|---|---|---|
| 6,193,695 B1 | 2/2001 | Rippstein, Jr. | |
| 6,280,418 B1 | 8/2001 | Reinhard et al. | |
| 6,387,078 B1 | 5/2002 | Gillespie | |
| 7,896,849 B2 | 3/2011 | Delay | |
| 8,196,614 B2 | 6/2012 | Kriheli | |
| 8,267,124 B2 | 9/2012 | Bowie | |
| 8,721,612 B2 | 5/2014 | Domkowski et al. | |
| 9,045,259 B2 | 6/2015 | Greter et al. | |
| 10,022,301 B2 | 7/2018 | Ivosevic et al. | |
| 2004/0054327 A1 | 3/2004 | Gillespie | |
| 2004/0186427 A1 | 9/2004 | Pok | |
| 2004/0199085 A1 | 10/2004 | Young et al. | |
| 2005/0240159 A1 | 10/2005 | Kito et al. | |
| 2006/0116644 A1 | 6/2006 | Norton | |
| 2006/0253074 A1 | 11/2006 | Thayer | |
| 2007/0013554 A1 | 1/2007 | Tyburski | |
| 2007/0179454 A1 | 8/2007 | Ziman et al. | |
| 2008/0277021 A1 | 11/2008 | Horppu et al. | |
| 2010/0218846 A1 | 9/2010 | Kriheli | |
| 2011/0295212 A1 | 12/2011 | Greter et al. | |
| 2012/0226157 A1* | 9/2012 | Hack | A61M 5/14546 600/432 |
| 2013/0116631 A1 | 5/2013 | Ziman et al. | |
| 2014/0171875 A1 | 9/2014 | Poncon | |
| 2014/0311624 A1 | 10/2014 | Eilertsen et al. | |
| 2015/0020919 A1 | 1/2015 | Wu et al. | |
| 2015/0297453 A1* | 10/2015 | Kim | A61J 1/2048 285/92 |
| 2015/0297881 A1* | 10/2015 | Sanders | A61J 1/2096 604/535 |

FOREIGN PATENT DOCUMENTS

| | | |
|---|---|---|
| EP | 2379162 B1 | 10/2013 |
| IL | 234746 | 3/2016 |
| IL | 237788 | 9/2016 |
| JP | S52129072 U | 10/1977 |
| JP | H08107921 A | 4/1996 |
| JP | H09173449 A | 7/1997 |
| JP | 2004097640 A | 4/2004 |
| JP | 2005021431 | 1/2005 |
| WO | 03072181 A1 | 9/2003 |
| WO | 2011122296 A1 | 10/2011 |
| WO | 2014/122643 A1 | 8/2014 |
| WO | 2014/181320 A1 | 11/2014 |

* cited by examiner

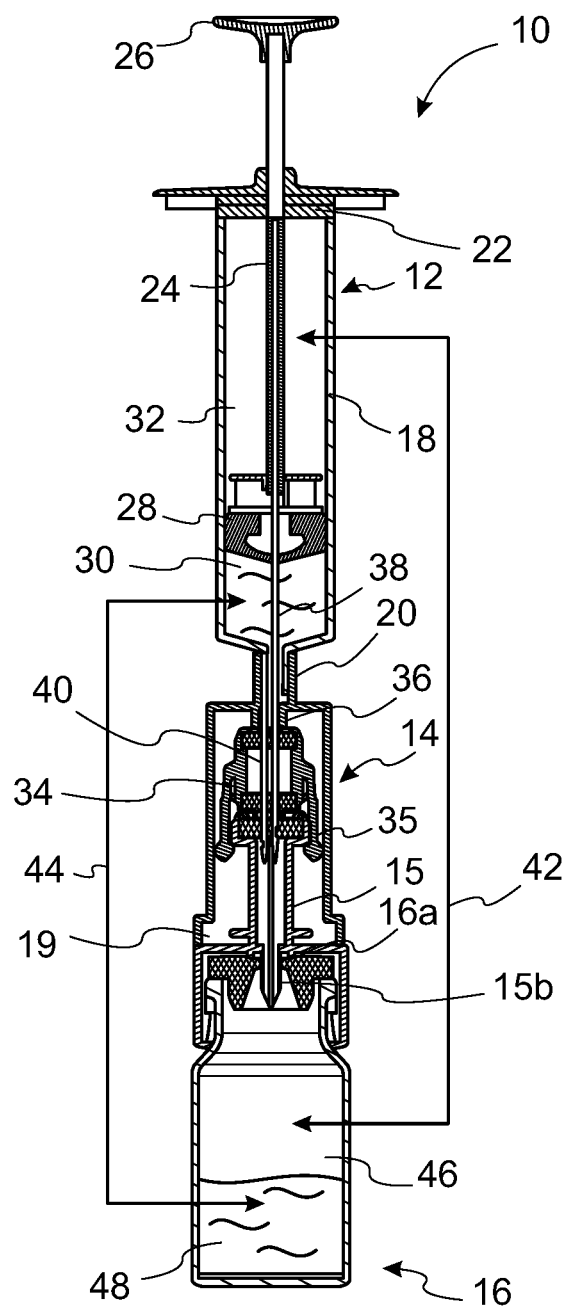
PRIOR ART
Fig. 1

Fig. 2a
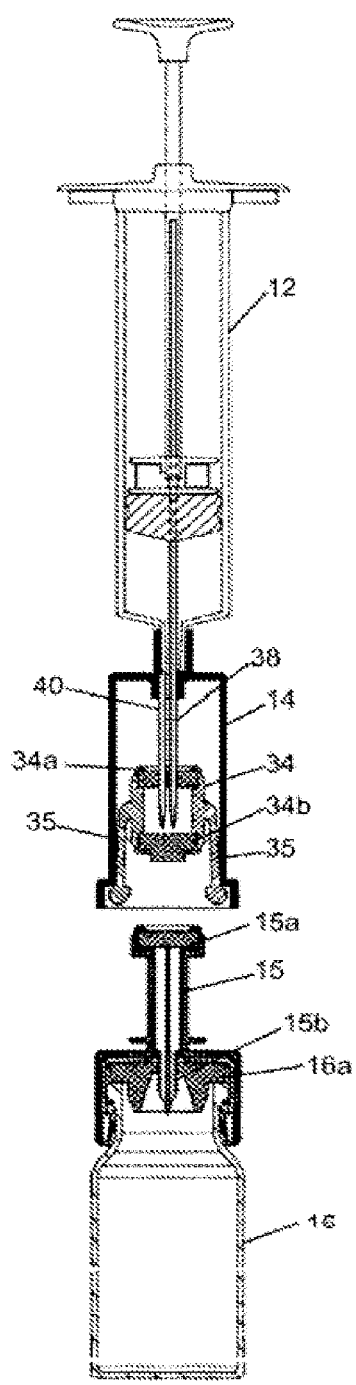
PRIOR ART
Fig. 2b
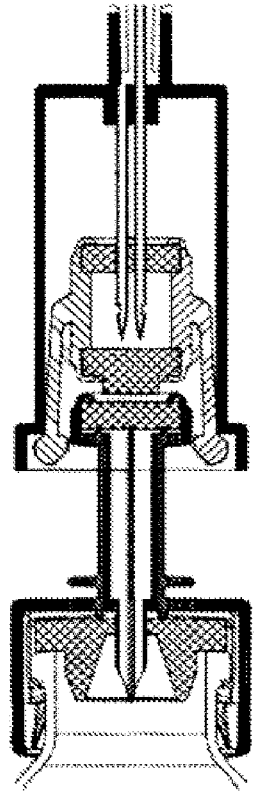
PRIOR ART
Fig. 2c
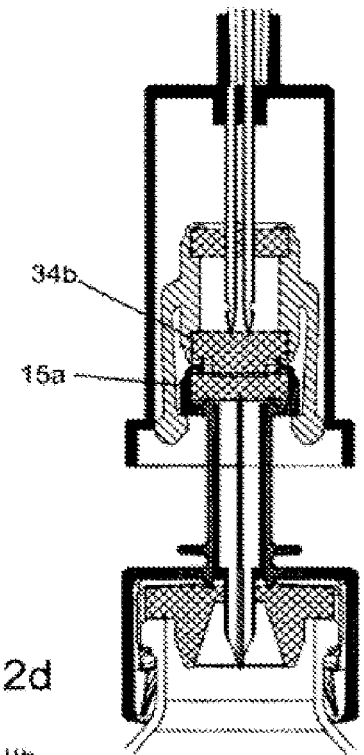
PRIOR ART
Fig. 2d
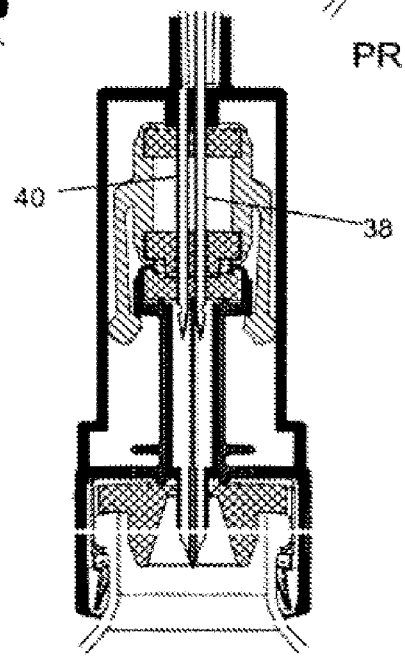
PRIOR ART

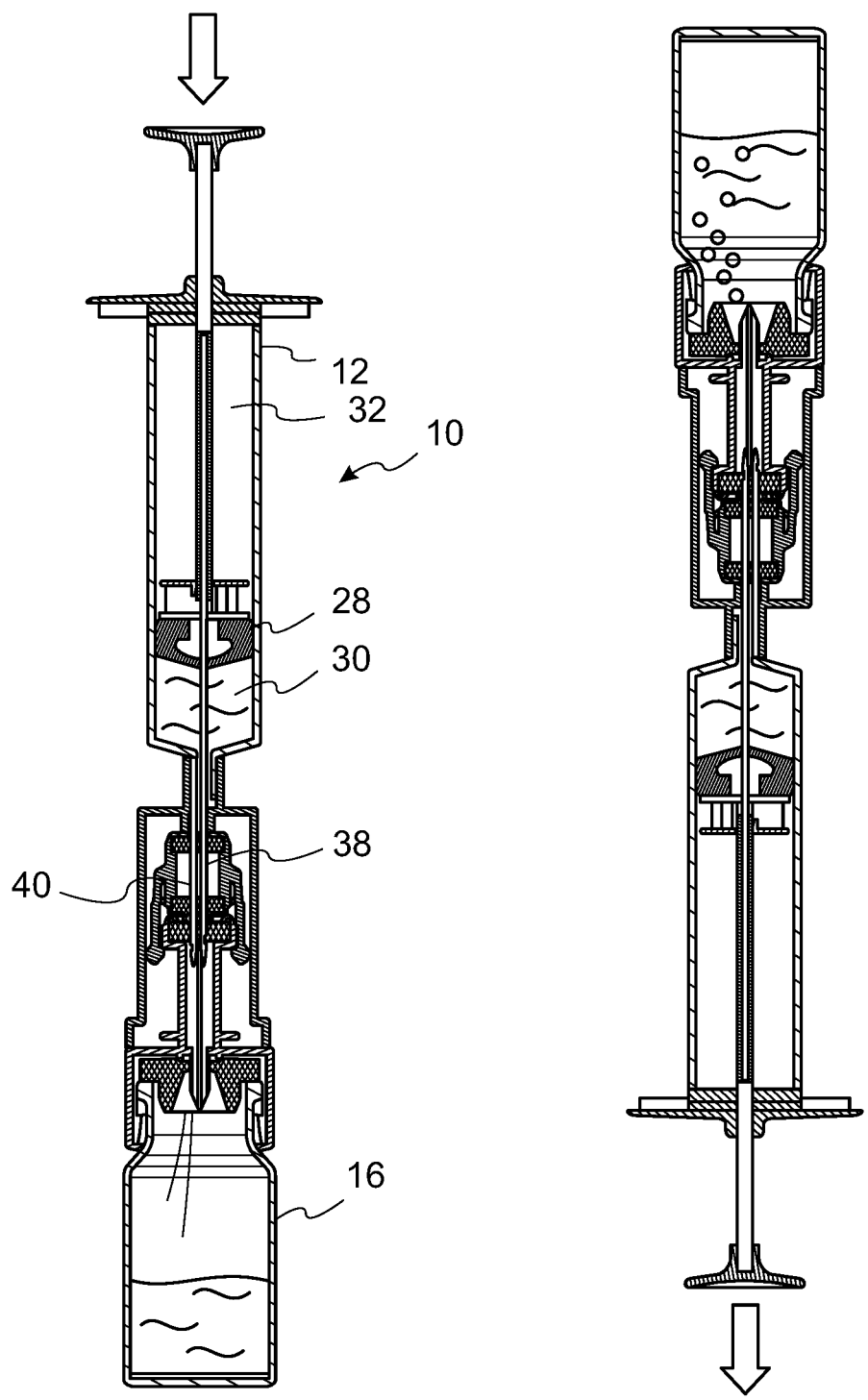
PRIOR ART
Fig. 3a
PRIOR ART
Fig. 3b

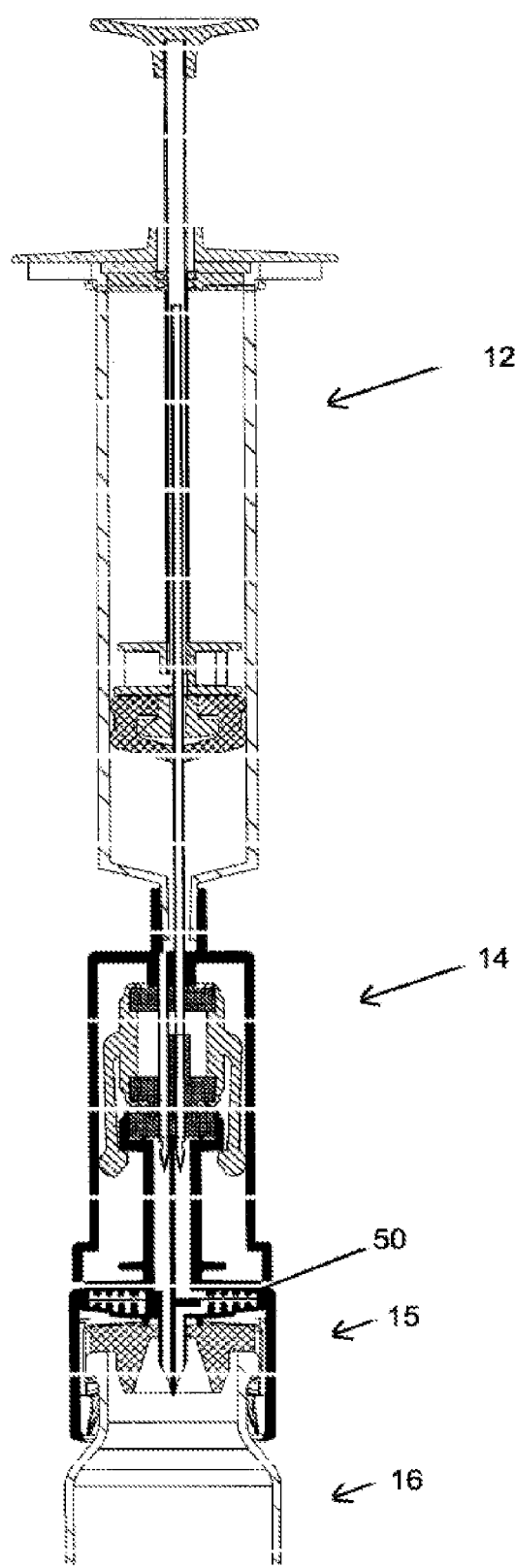
Fig. 4
PRIOR ART

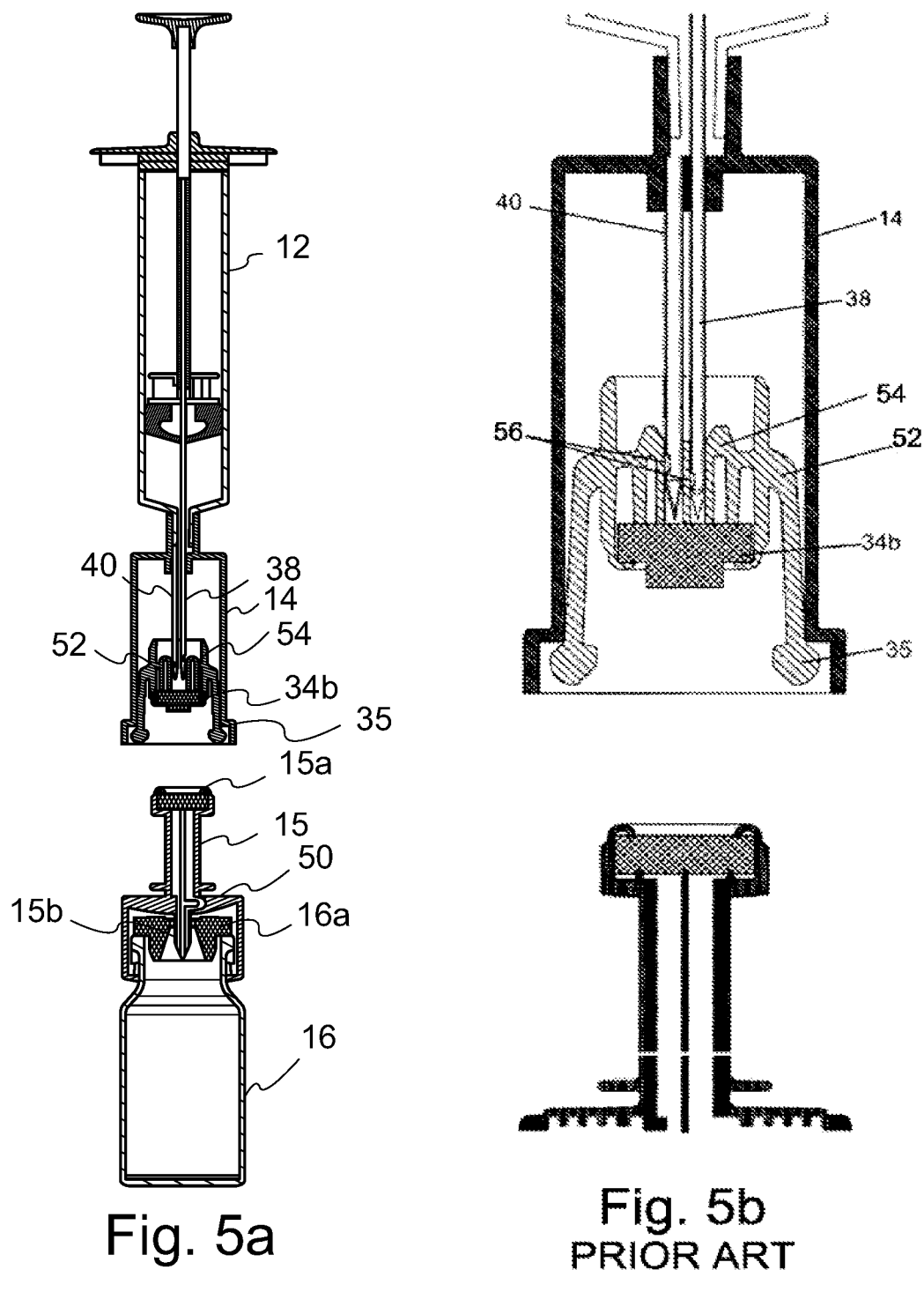
Fig. 5a
PRIOR ART
Fig. 5b
PRIOR ART

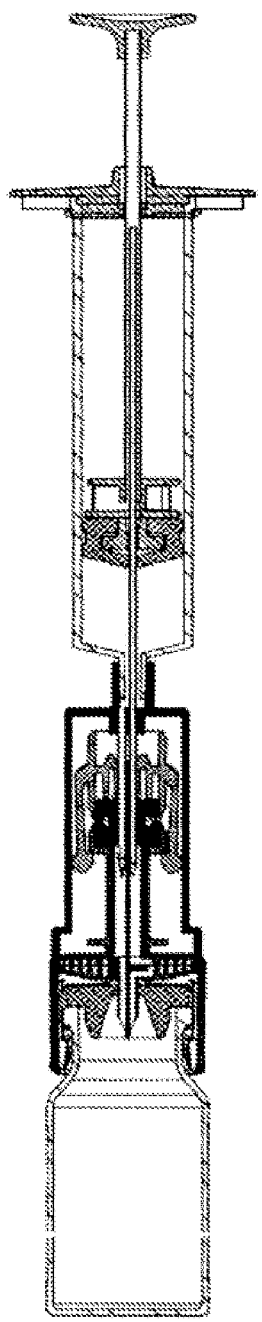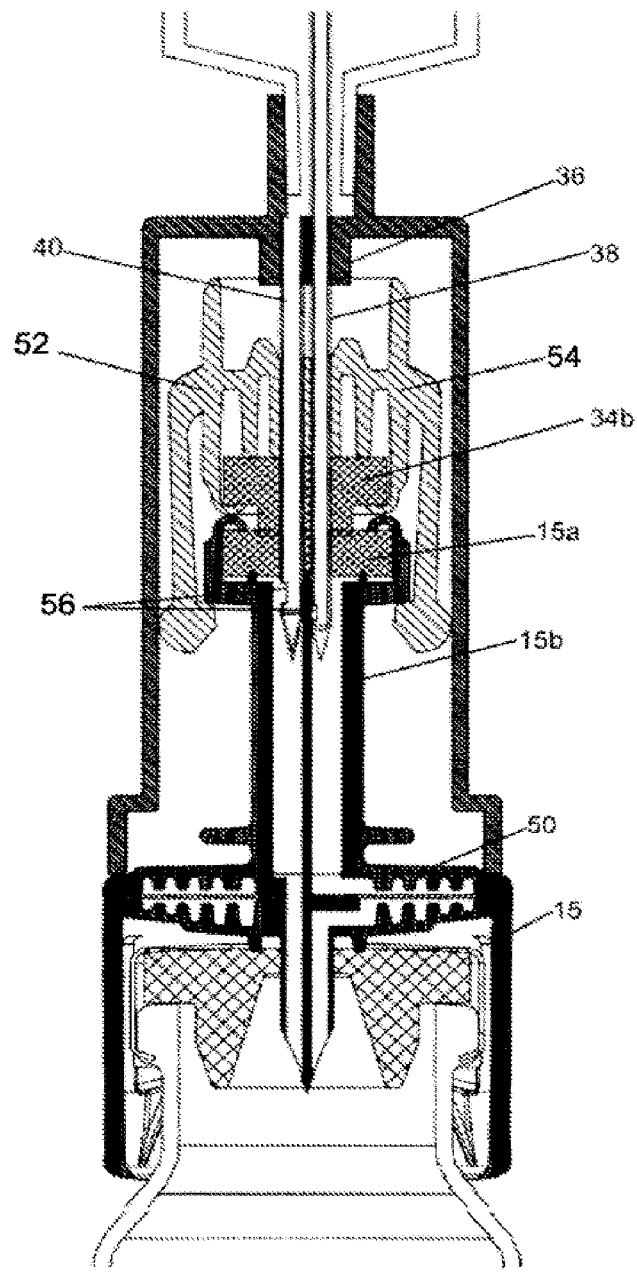
Fig. 6a
PRIOR ART
Fig. 6b
PRIOR ART

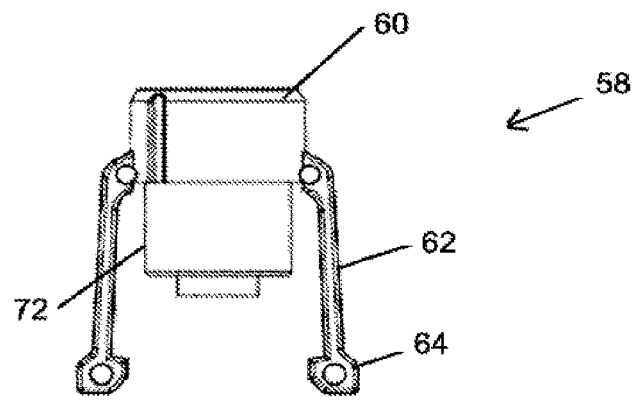
Fig. 7a
PRIOR ART
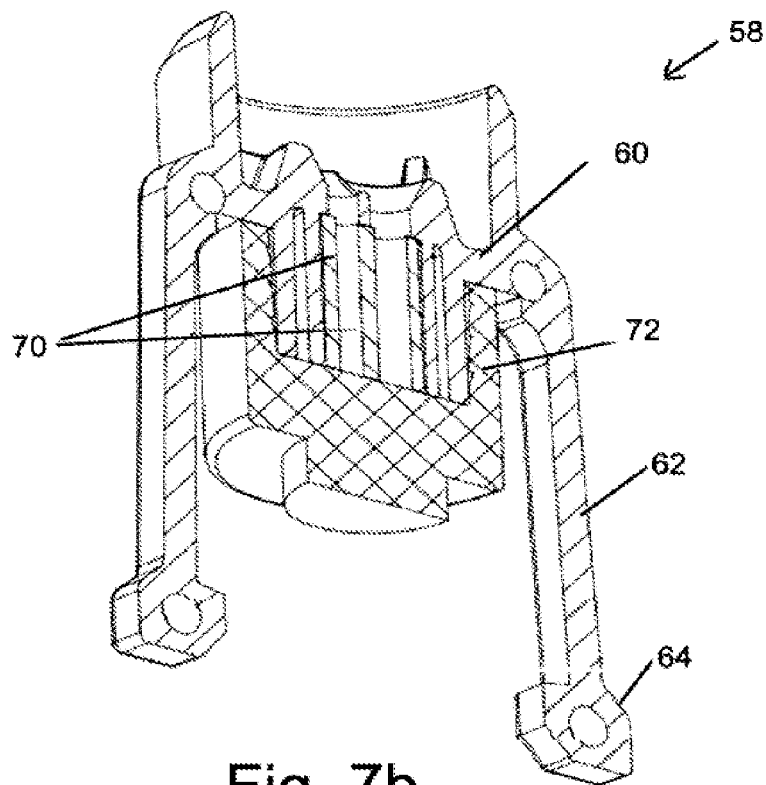
Fig. 7b
PRIOR ART

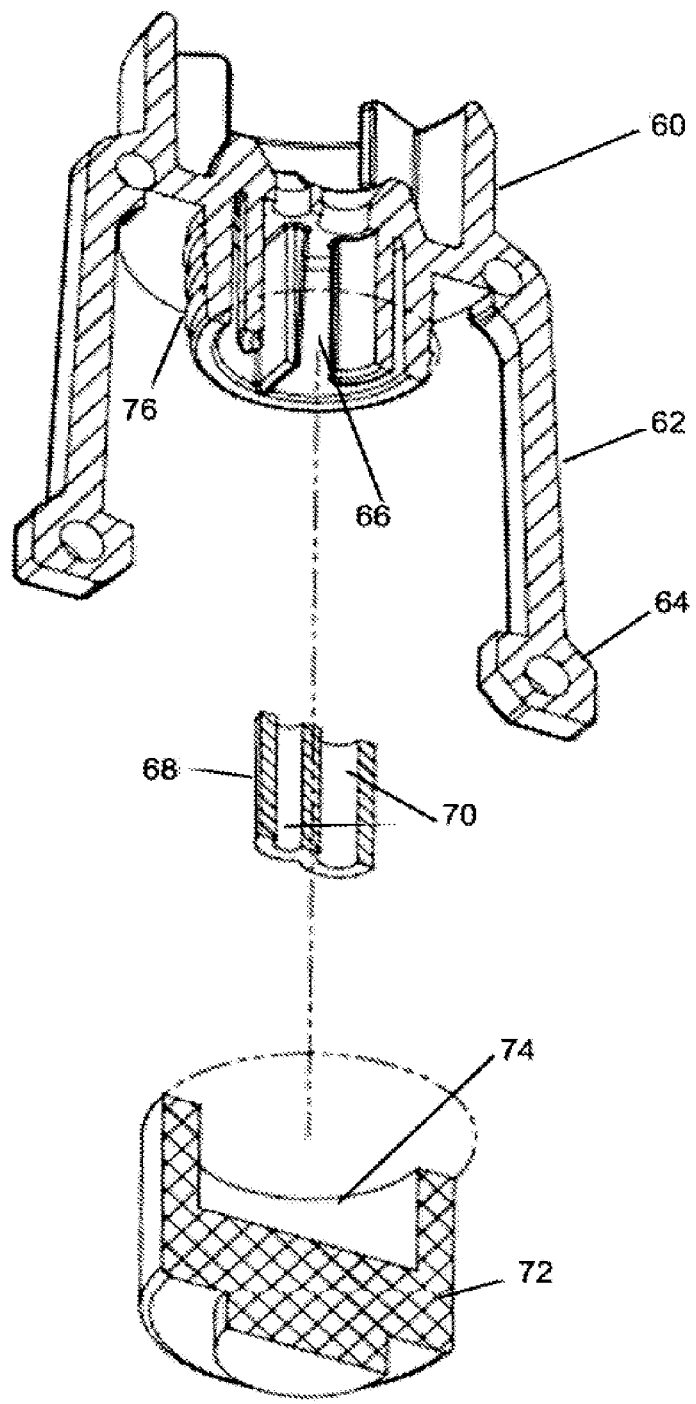
Fig. 7c
PRIOR ART

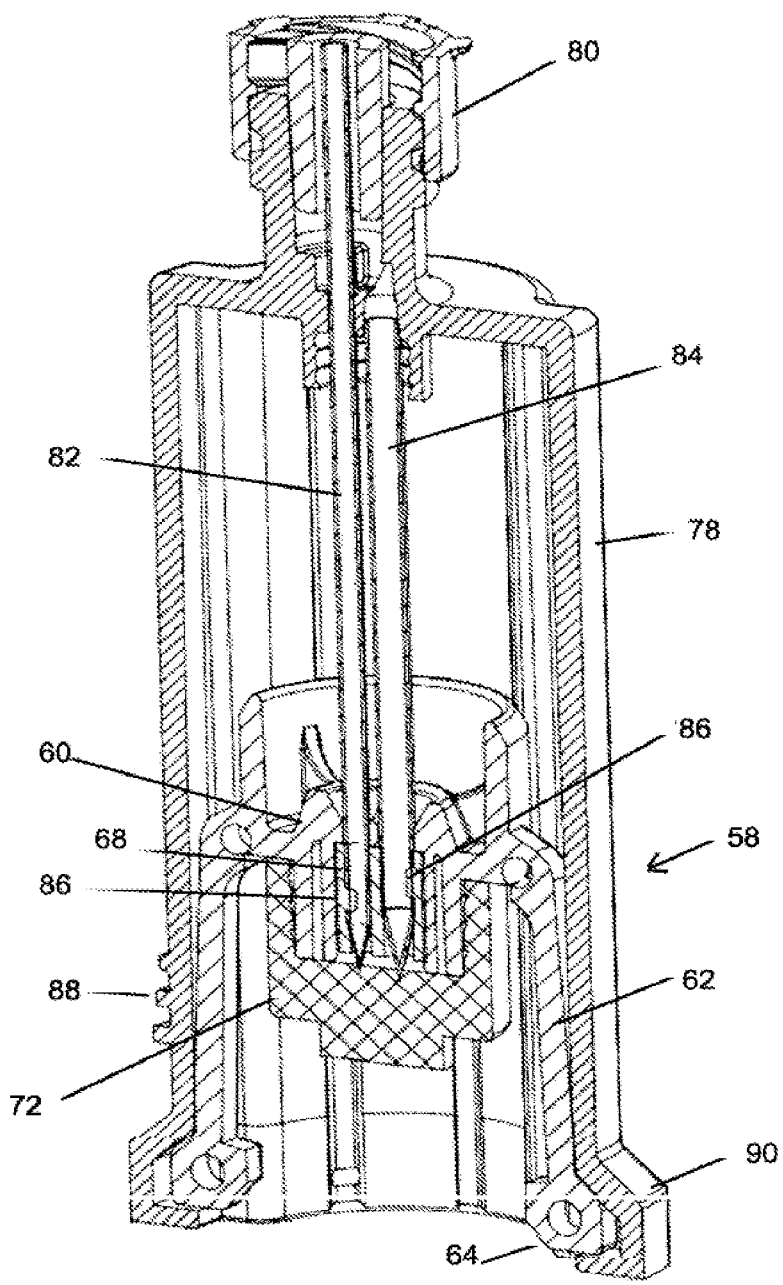
Fig. 7d
PRIOR ART

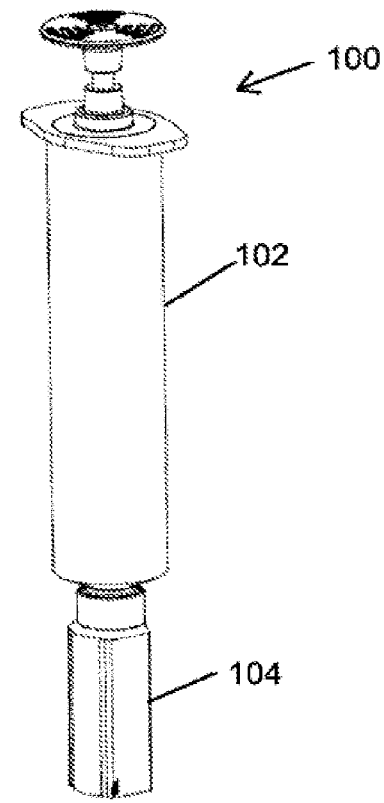
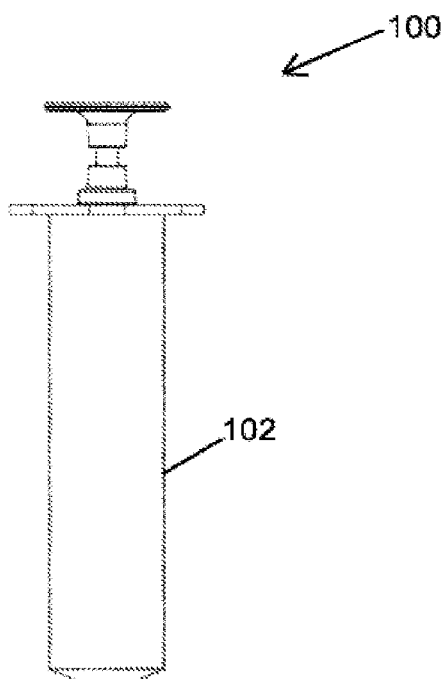
Fig. 8a
Fig. 8b

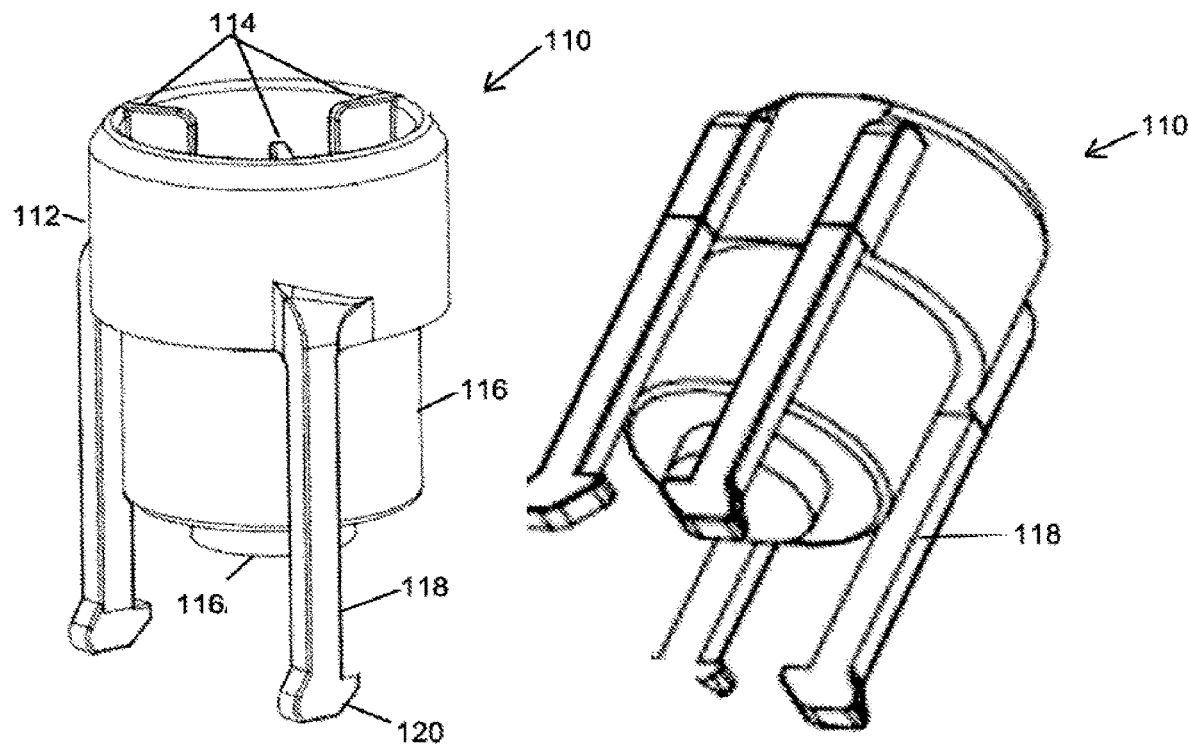
Fig. 9a                Fig. 9b
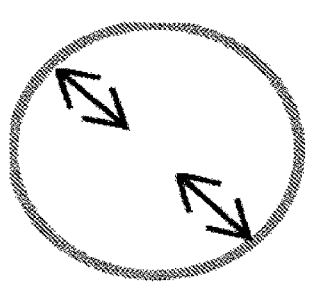
Fig. 10a
PRIOR ART
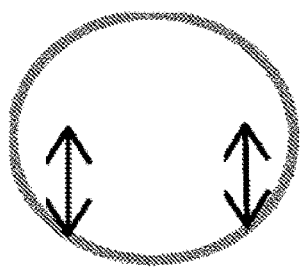
Fig. 10b

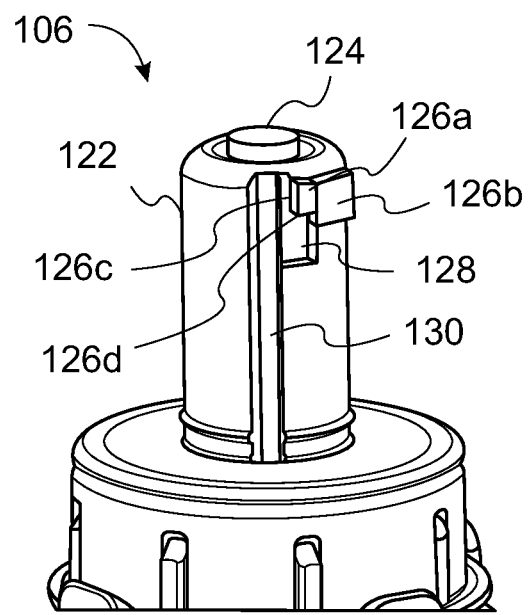 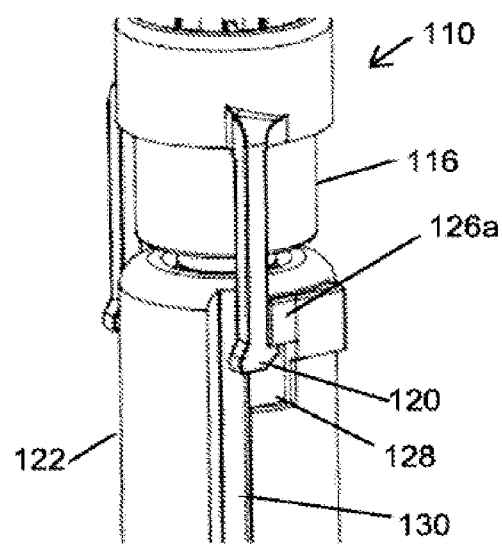
Fig. 11a          Fig. 11b
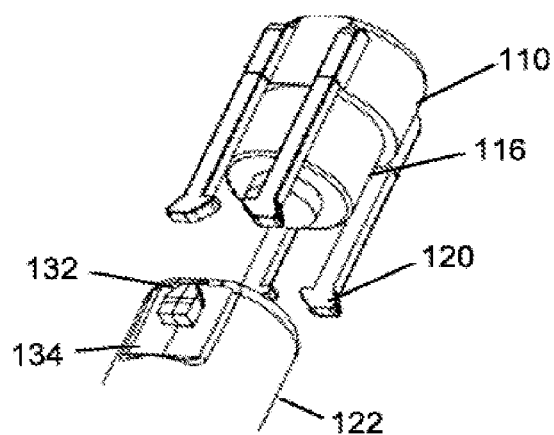 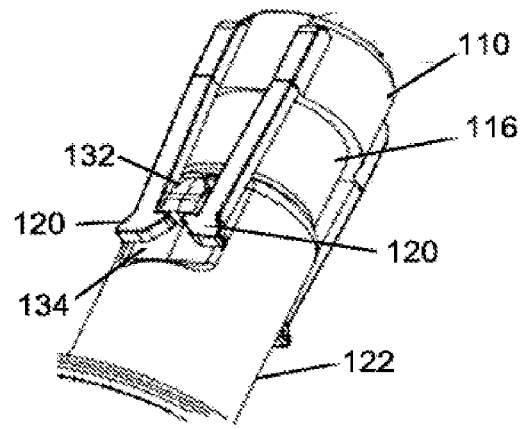
Fig. 12a          Fig. 12b

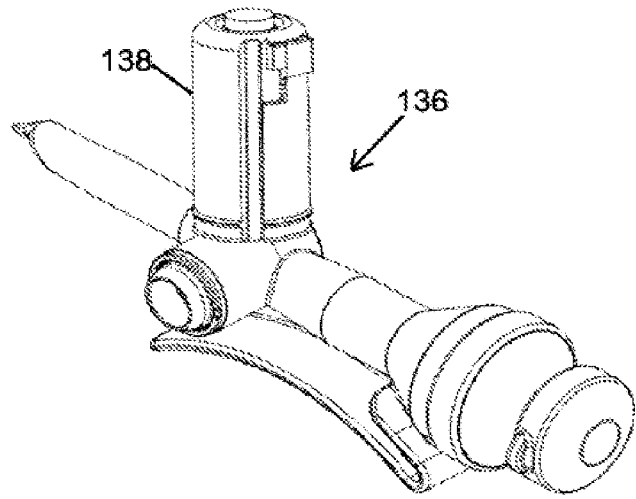
Fig. 13
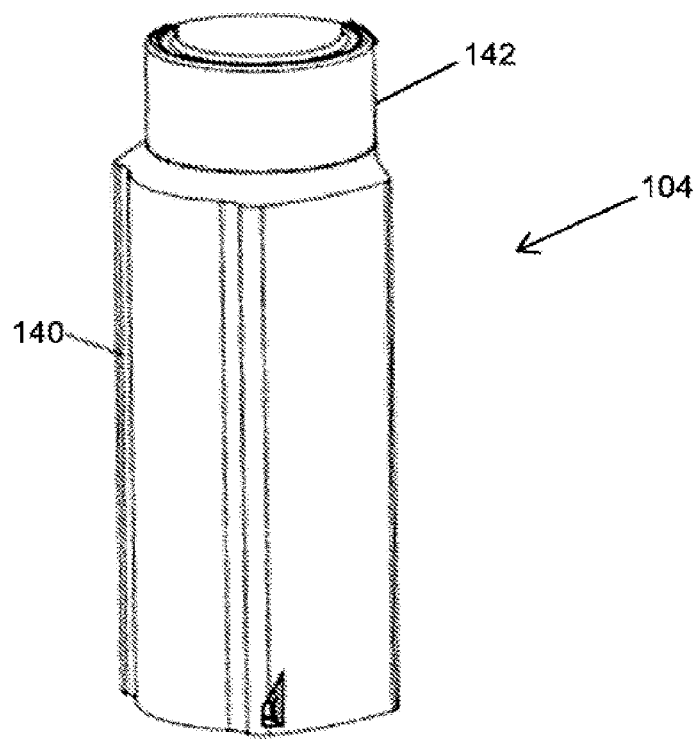
Fig. 14

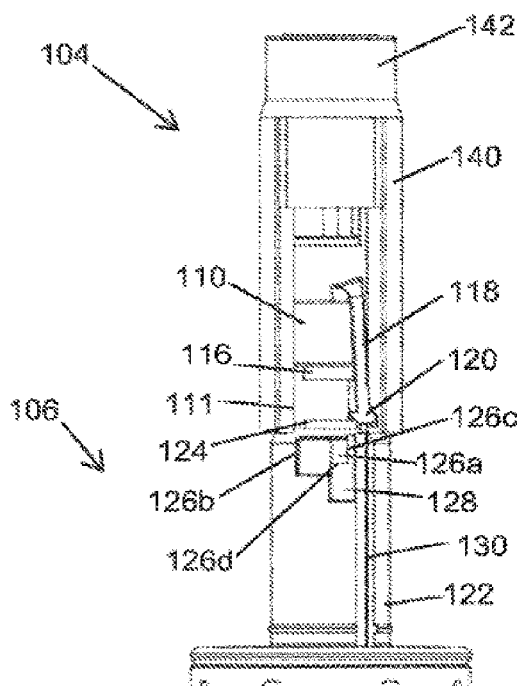
Fig. 15a
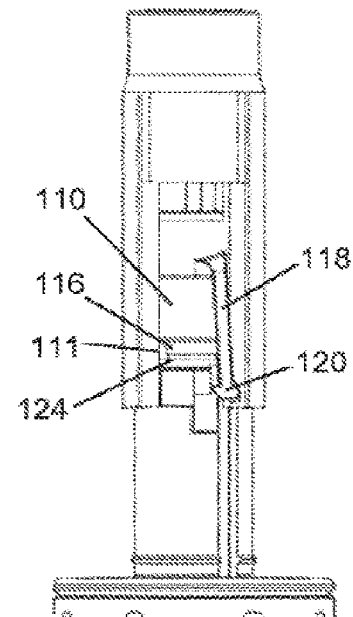
Fig. 15b
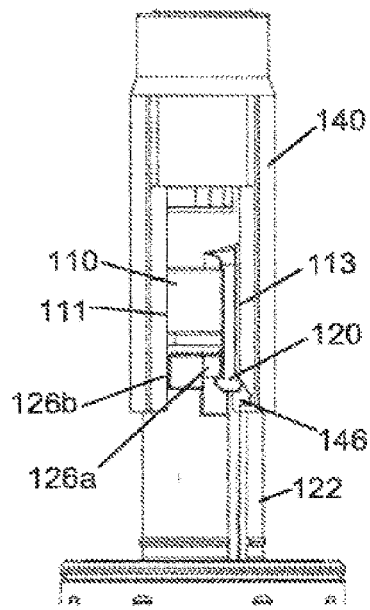
Fig. 15c
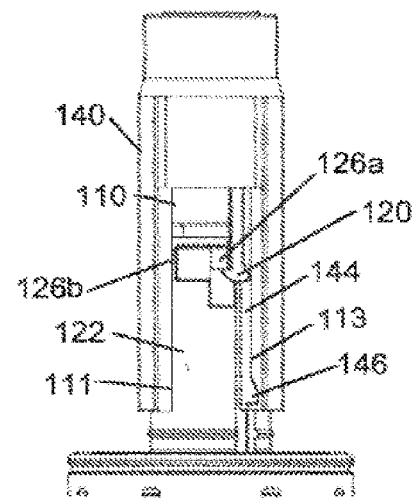
Fig. 15d

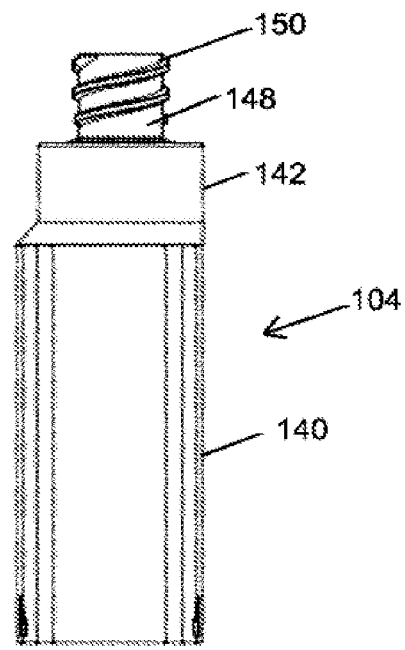
Fig. 16a
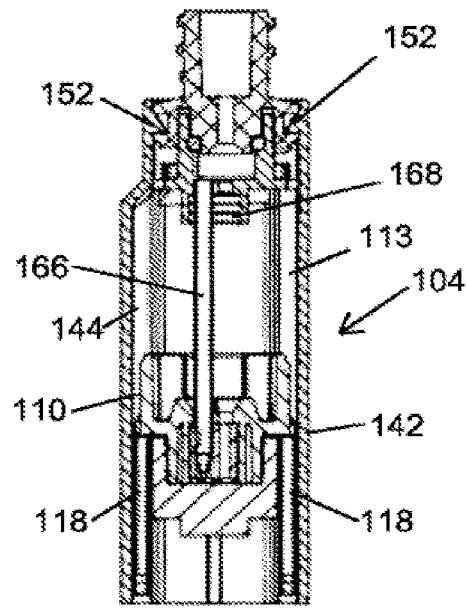
Fig. 16b
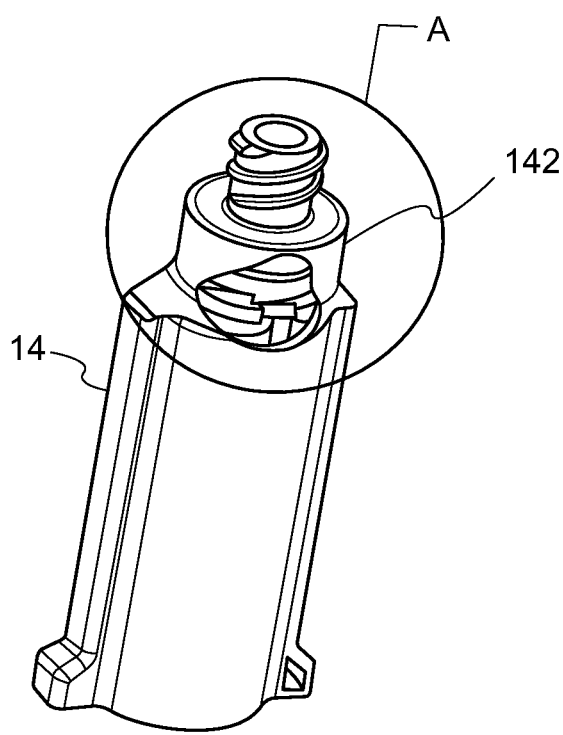
Fig. 17a
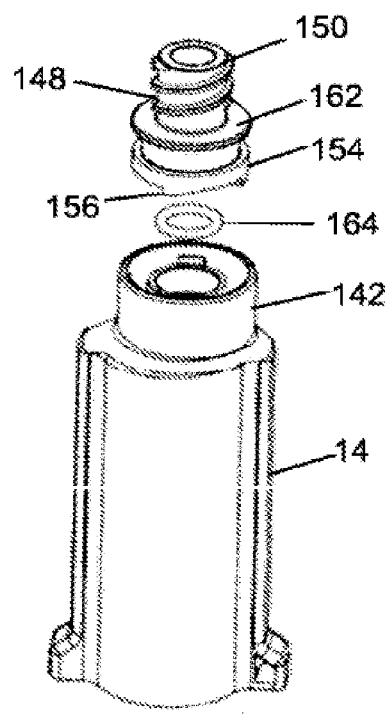
Fig. 17b

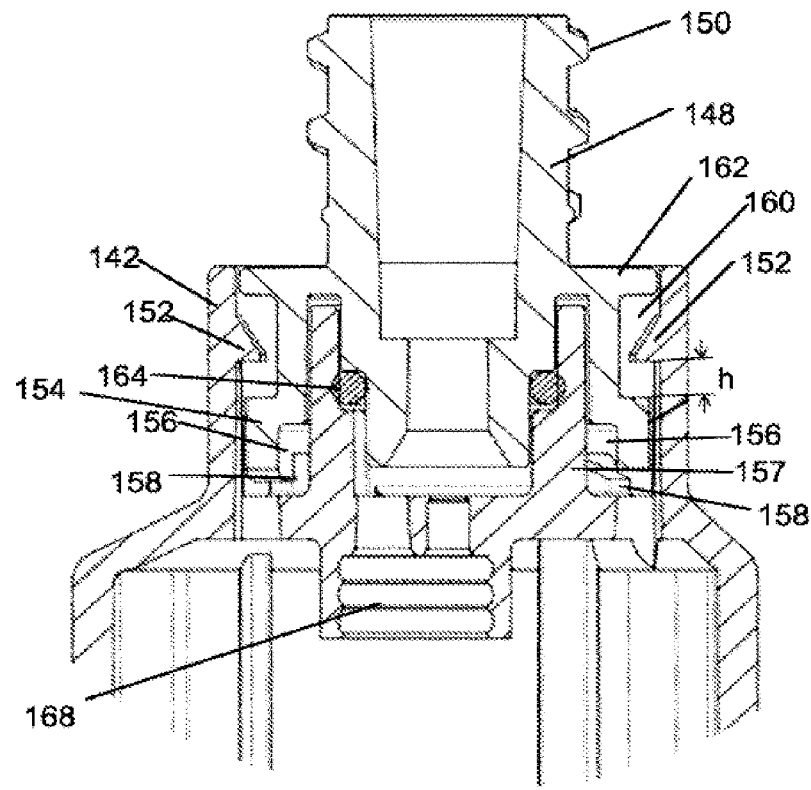
Fig. 18
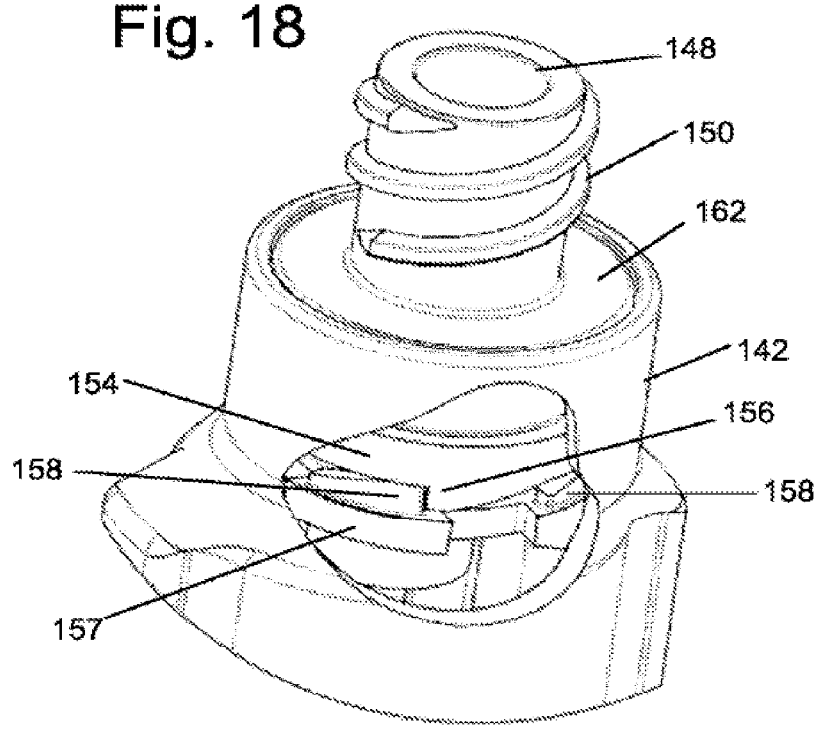
Fig. 19

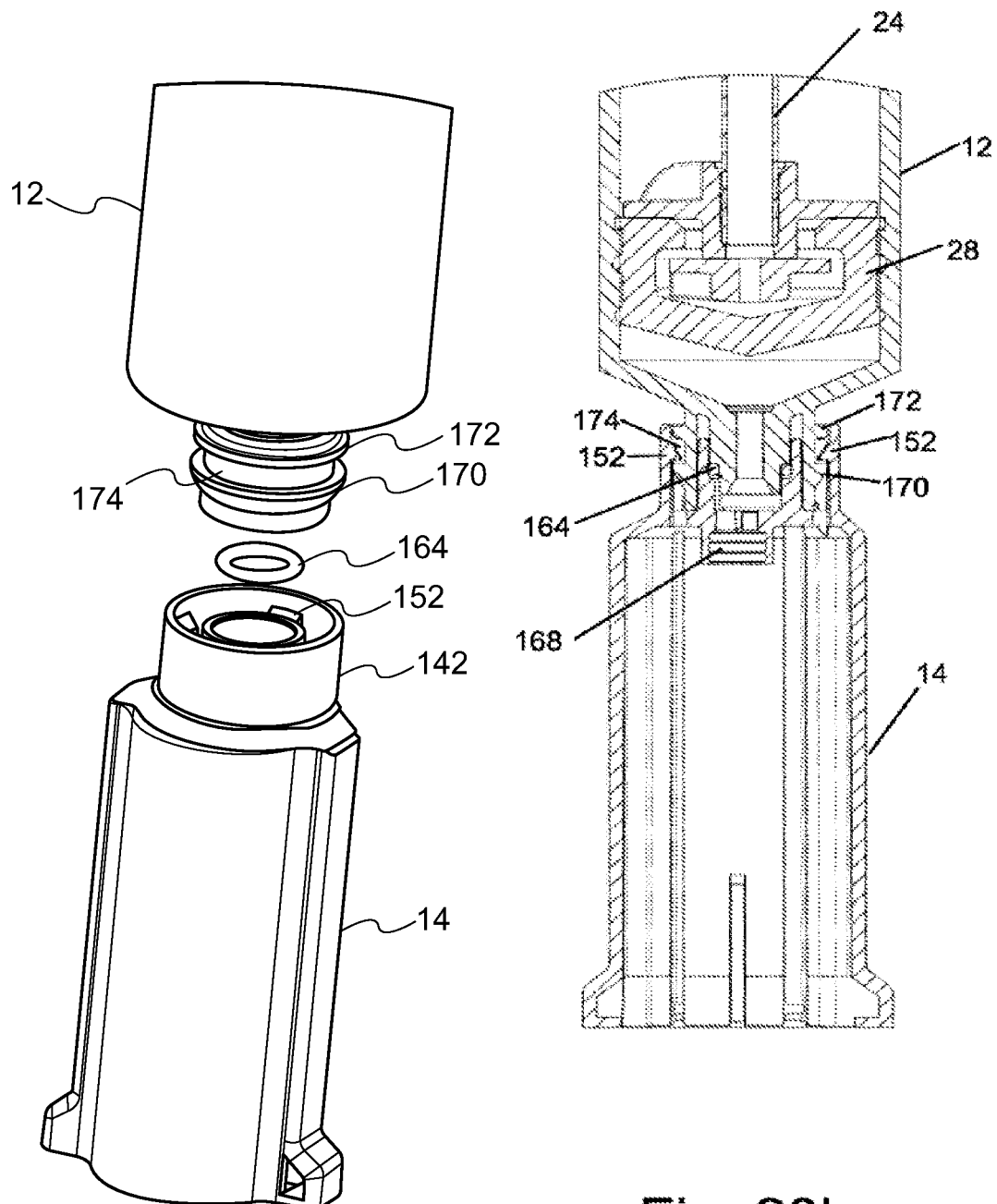
Fig. 20a
Fig. 20b

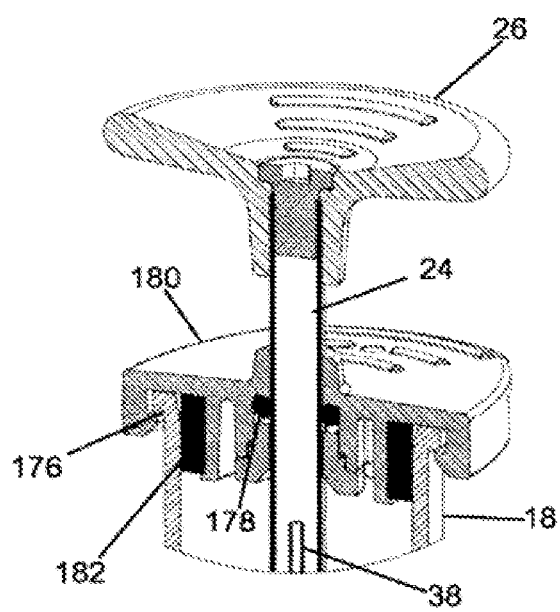
Fig. 21a
PRIOR ART
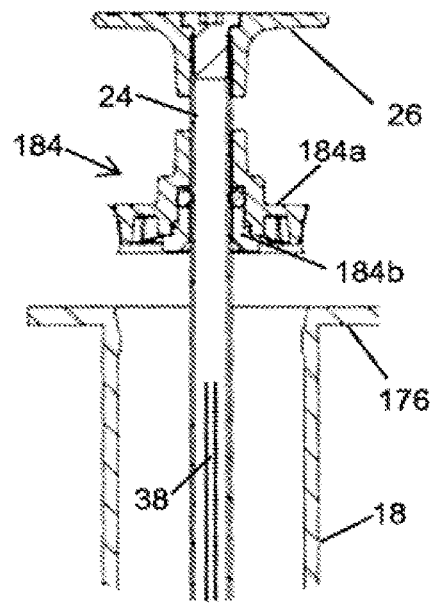
Fig. 21b
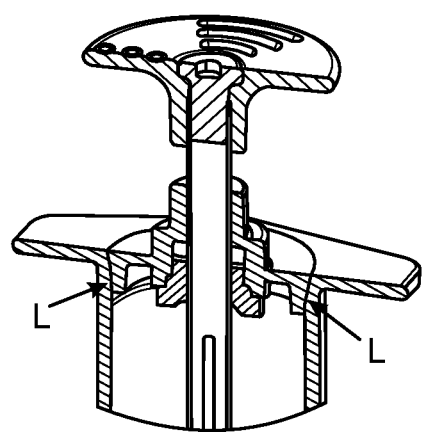
Fig. 21c
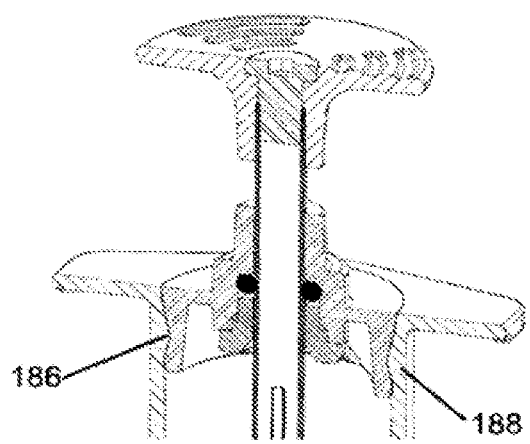
Fig. 21d

COMPONENTS OF A FLUID TRANSFER APPARATUS

FIELD OF THE INVENTION

The present invention relates to the field of fluid transfer apparatuses. Particularly, the invention relates to apparatus for the contamination-free transfer of a hazardous drug from one container to another or to a patient. More particularly, the invention relates to improvements to syringes and to connectors and adapters that are used in fluid transfer apparatuses.

BACKGROUND OF THE INVENTION

Advances in medical treatment and improved procedures constantly increase the need for improved valves and connectors. The demands relating to a variety of types, quality, needle safety, microbial ingress prevention and leak prevention are constantly growing. Additionally, advances in sampling or dose dispensing technologies, automated and manual, aseptic or non-aseptic applications, call for new safe concealing solutions for the sampling needle. One extremely demanding application exists in the field where medical and pharmacological personnel that are involved in the preparation and administration of hazardous drugs suffer the risk of being exposed to drugs and to their vapors, which may escape to the surroundings. As referred to herein, a "hazardous drug" is any injectable material the contact with which, or with the vapors of which, may constitute a health hazard. Illustrative and non-limitative examples of such drugs include, inter aka, cytotoxins, antiviral drugs, chemotherapy drugs, antibiotics, and radiopharmaceuticals, such as herceptin, cisplatinum, fluorouracil, leucovorin, paclitaxel, etoposide, cyclophosphamideand neosar, or a combination thereof, in a liquid, solid, or gaseous state.

Hazardous drugs in liquid or powder form are contained within vials, and are typically prepared in a separate room by pharmacists provided with protective clothing, a mouth mask, and a laminar flow safety cabinet. A syringe provided with a cannula, i.e. a hollow needle, is used for transferring the drug from a vial. After being prepared, the hazardous drug is added to a solution contained in a bag which is intended for parenteral administration, such as a saline solution intended for intravenous administration.

Since hazardous drugs are toxic, direct bodily contact thereto, or exposure to even micro-quantities of the drug vapors, considerably increases the risk of developing health problems that can result in fatalities such as skin cancer, leukemia, liver damage, malformation, miscarriage and premature birth. Such exposure can take place when a drug containing receptacle, such as a vial, bottle, syringe, and intravenous bag, is subjected to overpressure, resulting in the leakage of fluid or air contaminated by the hazardous drug to the surroundings. Exposure to a hazardous drug also results from a drug solution remaining on a needle tip, on a vial or intravenous bag seal, or by the accidental puncturing of the skin by the needle tip. Additionally, through the same routes of exposure, microbial contaminants from the environment can be transferred into the drug and fluids; thus eliminating the sterility with possibly fatal consequences.

U.S. Pat. Nos. 8,196,614 and 8,267,127 to the inventor of the present invention describe closed system liquid transfer devices designed to provide contamination-free transfer of hazardous drugs. FIG. 1 and FIGS. 3a to 3b are schematic cross-sectional views of an apparatus 10 for transferring hazardous drugs without contaminating the surroundings, according to one embodiment of the invention described in U.S. Pat. No. 8,196,614. The main features of this apparatus that are relevant to the present invention will be described herein. Additional details can be found in the aforementioned patent.

The proximal section of apparatus 10 is a syringe 12, which is adapted to draw or inject a desired volume of a hazardous drug from a fluid transfer component, e.g. a vial 16 or an intravenous (IV) bag in which it is contained and to subsequently transfer the drug to another fluid transfer component. At the distal end of syringe 12 is connected a connector section 14, which is in turn connected to vial 16 by means of vial adapter 15.

Syringe 12 of apparatus 10 is comprised of a cylindrical body 18 having a tubular throat 20 that has a considerably smaller diameter than body 18, an annular rubber gasket or stopper assembly 22 fitted on the proximal end of cylindrical body 18, hollow piston rod 24 which sealingly passes through stopper 22, and proximal piston rod cap 26 by which a user can push and pull piston rod 24 up and down through stopper 22. A piston 28 made of an elastomeric material is securely attached to the distal end of piston rod 24. Cylindrical body 18 is made of a rigid material, e.g. plastic.

Piston 28, which sealingly engages the inner wall of, and is displaceable with respect to, cylindrical body 18 defines two chambers of variable volume: a distal liquid chamber 30 between the distal face of piston 28 and connector section 14 and a proximal air chamber 32 between the proximal face of piston 28 and stopper 22.

Connector section 14 is connected to the throat 20 of syringe 12 by means of a collar which proximally protrudes from the top of connector section 14 and surrounds throat 20. Note that embodiments of the apparatus do not necessarily have a throat 20. In these embodiments syringe 12 and connector section 14 are formed together as a single element at the time of manufacture, or permanently attached together, e.g. by means of glue or welding, or formed with a coupling means, such as threaded engagement or a Luer connector. The connector section 14 comprises a double membrane seal actuator which is moveable in a reciprocating manner from a normal, first configuration in which the needles are concealed when the double membrane seal actuator is disposed in a first, distal position and a second position in which the needles are exposed when the double membrane seal actuator is proximally displaced. Connector section 14 is adapted to be releasably coupled to another fluid transfer component, which can be any fluid container with a standard connector such as a drug vial, intravenous bag, or an intravenous line to produce a "fluid transfer assembly", through which a fluid is transferred from one fluid transfer component to another.

Connector section 14 comprises a cylindrical, hollow outer body; a distal shoulder portion 19, which radially protrudes from the body and terminates at the distal end with an opening through which the proximal end of a fluid transfer component is inserted for coupling; a double membrane seal actuator 34, which is reciprocally displaceable within the interior of the body; and one or more resilient arms 35 serving as locking elements, which are connected at a proximal end thereof to an intermediate portion of a cylindrical actuator casing that contains double membrane seal actuator 34. Two hollow needles that function as air conduit 38 and liquid conduit 40 are fixedly retained in needle holder 36, which protrudes into the interior of connector section 14 from a central portion of the top of connector section 14.

Conduits 38 and 40 distally extend from needle holder 36, piercing the upper membrane of actuator 34. The distal ends of conduits 38 and 40 have sharp pointed ends and apertures through which air and liquid can pass into and out of the interiors of the conduits respectively as required during a fluid transfer operation. The proximal end of air conduit 38 extends within the interior of proximal air chamber 32 in syringe 12. In the embodiment shown in FIG. 1, air conduit 38 passes through piston 28 and extends inside of hollow piston rod 24. Air flowing through conduit 38 enters/exits the interior of piston rod 24 and exits/enters to air chamber 32 through an aperture formed at the distal end of piston rod 24 just above piston 28. The proximal end of liquid conduit 40 terminates at the top of or slightly proximally from the top of needle holder 36, so that the liquid conduit will be in fluid communication with the distal liquid chamber 30 via the interior of throat 20 of syringe 12.

Double membrane seal actuator 34 comprises a cylindrical casing that holds a proximal disc shaped membrane 34a having a rectangular cross-section and a two level distal membrane 34b having a T-shaped cross-section with disc shaped proximal portion and a disc shaped distal portion disposed radially inwards with respect to the proximal portion. The distal portion of the distal membrane 34b protrudes distally from actuator 34. Two or more equal length resilient elongated arms 35 are attached to the distal end of the casing of actuator 34. The arms terminate with distal enlarged elements. When actuator 34 is in a first position, the pointed ends of conduits 38 and 40 are retained between the proximal and distal membranes, isolating the ends of conduits 38 and 40 from the surroundings, thereby preventing contamination of the interior of syringe 12 and leakage of a harmful drug contained within its interior to the surroundings.

Vial adapter 15 is an intermediate connection that is used to connect connector section 14 to a drug vial 16 or any other component having a suitably shaped and dimensioned port. Vial adapter 15 comprises a disk shaped central piece to which a plurality of circumferential segments, formed with a convex lip on the inner face thereof for facilitating securement to a head portion of a vial 16, are attached at the circumference of the disk and pointing distally away from it and a longitudinal extension projecting proximally from the other side of the disk shaped central piece. Longitudinal extension fits into the opening at the distal end of connector section 14 to allow transfer of the drug as described herein below. The longitudinal extension terminates proximally with a membrane enclosure having a diameter larger than that of the extension. A central opening in the membrane enclosure retains and makes accessible a membrane 15a.

Two longitudinal channels, which are internally formed within the longitudinal extension and that extend distally from the membrane in the membrane enclosure, are adapted to receive conduits 38 and 40, respectively. A mechanical guidance mechanism is provided to insure that the conduits 38 and 40 will always enter their designated channel within the longitudinal extension when connector section 14 is mated with vial adapter 15. The longitudinal extension terminates distally with a spike element 15b which protrudes distally. The spike element is formed with openings in communication with the internally formed channels, respectively and openings at its distal pointed end.

Vial 16 has an enlarged circular head portion attached to the main body of the vial with a neck portion. In the center of the head portion is a proximal seal 16a, which is adapted to prevent the outward leakage of a drug contained therein. When the head portion of vial 16 is inserted into the collar portion of vial adapter 15 and a distal force is applied to vial adapter 15, the spike element 15b of the connector section 14 pierces the seal 16a of vial 16, to allow the internal channels in the connector section 14 to communicate with the interior of drug vial 16. When this occurs, the circumferential segments at the distal end of the collar portion of the connector section are securely engaged with the head portion of vial 16. After the seal of vial 16 is pierced it seals around the spike preventing the outward leakage of the drug from the vial. At the same time the tops of the internal channels in vial adapter 15 are sealed by the membrane 15a at the top of vial adapter 15, preventing air or drug from entering or exiting the interior of vial 16.

The procedure for assembling drug transfer apparatus 10 is carried out as shown in FIGS. 2a to 2d: Step 1—After the vial 16 and vial adapter 15 have been joined together, with spike element 15b penetrating proximal seal 16a of the vial, the membrane enclosure 15a of vial adapter 15 is positioned close to the distal opening of connector section 14, as shown in FIG. 2a. Step 2—A double membrane engagement procedure is initiated by distally displacing the body of connector section 14 with an axial motion until the membrane enclosure and longitudinal extension of vial adapter 15 enters the opening at the distal end of the connector section 14, as shown in FIG. 2b. Step 3—the distal membrane 34b of actuator 34 is caused to contact and be pressed against the stationary membrane 15a of vial adapter 15 by additional distal displacement of the body of the connector section 14. After the membranes are pressed tightly together the enlarged elements at the ends of the arms of the connector section 14 are squeezed into the more narrow proximal section of connector section 14 thereby holding the membranes pressed together and engaged around the longitudinal extension and under the membrane enclosure of vial adapter 15, as shown in FIG. 2c, thereby preventing disengagement of the double membrane seal actuator 34 from vial adapter 15. Step 4—Additional distal displacement of the body of connector section 14, as shown in FIG. 2d, causes actuator 34 to move proximally relative to the body of the connector section 15 until the tips of conduits 38 and 40 pierce the distal membrane of actuator 34 and the membrane at the top of vial adapter 15 and are in fluid communication with the interior of vial 16. These four steps are performed by one continuous axial motion as connector section 14 is distally displaced relative to the vial adapter 15, and they will be reversed to separate connector section 14 from vial adapter 15 by pulling connector section 14 and vial adapter 15 apart. It is important to emphasize that the procedure is described herein as comprising four separate steps, however this is for ease in describing the procedure only. It is to be realized that in actual practice the secured double membrane engagement (and disengagement) procedure using the present invention is carried out using a single smooth axial movement.

After drug transfer assembly 10 shown in FIG. 1 is assembled as described hereinabove with reference to FIGS. 2a to 2d, the piston rod 24 can be moved to withdraw liquid from vial 16 or to inject liquid from the syringe into the vial. The transfer of liquid between the distal liquid chamber 30 in the syringe 12 and liquid 48 in the vial 16 and transfer of air between the proximal air chamber 32 in the syringe 12 and air 46 in the vial 16 takes place by an internal pressure equalization process in which the same volumes of air and liquid are exchanged by moving through separate channels symbolically shown in FIG. 1 by paths 42 and 44 respectively. This is a closed system which eliminates the possibility of exchange of air or liquid drops or vapor between the interior of assembly 10 and the surroundings.

FIG. 3a schematically shows injection of a liquid into a vial. To inject liquid contained in the liquid chamber 30 of syringe 12 into the vial 16 the drug transfer assembly 10 must be held vertically with the vial at the bottom in an upright position as shown in FIG. 3a. Pushing piston 28 distally pushes the liquid out of liquid chamber 30 through conduit 40 into vial 16. Simultaneously, as the volume of liquid chamber 30 is reduced by the distally moving piston, the volume of air chamber 32 is increased. This creates a temporary state of negative pressure in the air chamber and therefore air (or an inert gas) inside vial 16 will be sucked through conduit 38 into air chamber 32. Additionally and simultaneously, as the liquid is added to the vial, the volume available for the air in the vial is reduced creating a temporary state of positive pressure, therefore the air is forced from the vial 16 through conduit 38 into air chamber 32, thus equalizing the pressures in the transfer assembly 10 and equilibrium is reached when piston 28 stops moving.

FIG. 3b schematically shows withdrawal of liquid from a vial. To withdraw liquid from the vial 16 and transfer it into the liquid chamber 30 of syringe 12 the drug transfer assembly 10 must be inverted and held vertically with the vial 16 in an upside-down position as shown FIG. 3b. For this operation, when apparatus 10 is assembled and the piston 28 in syringe 12 is pulled in the proximal direction, a state of negative pressure is created in liquid chamber 30 and liquid is sucked into it through conduit 40. Simultaneously the volume of air chamber 32 is reduced and air is forced out of it through conduit 38 into the vial (in FIG. 3b are shown the air bubbles created by the air entering the vial from air chamber 40). As described in FIGS. 3a and 3b this simultaneous transfer and replacing of equal volumes of gas and liquids respectively inside syringe and vial constitutes the closed system equalization system.

Despite the care that was taken to separate air path 42 from liquid path 44 there are two locations in the prior art assembly described in U.S. Pat. No. 8,196,614 in which these paths intersect under certain conditions allowing for the possibility of liquid to travel through the air conduit from the distal liquid chamber 30 or vial 16 to the proximal air chamber.

Specifically, in the prior art apparatus described in U.S. Pat. No. 8,196,614 there is a direct connection between the air and liquid channels:

A. inside the double membrane seal actuator 34, when the syringe 12 and attached connection section 14 are not connected to any other fluid transfer component; and
B. inside the vial 16 at the tip of the spike, when the apparatus 10 is assembled as shown in FIG. 1.

When part of the liquid does accidently find its way into the air chamber of the syringe, in addition to the obvious problems of esthetics, additional time consuming working steps become necessary to retrieve the drug and correct the dosage.

An example of a scenario when situation A is relevant is when the syringe contains liquid and is being handled, for example when being transported from the pharmacy to the ward. At such a time the piston rod might be accidentally pushed causing some of the drug to migrate to the proximal air chamber above the piston from where it cannot be expelled from the syringe. In such case the plunger needs to be pulled back in order to retrieve the drug, which is an extra work step and the wet residuals in the air chamber 32 cause an aesthetic problem.

An example of a scenario when situation B is relevant is when, during withdrawal of a liquid drug from a vial which is in a typical upside-down position, a bubble of air is seen to enter the liquid chamber of the syringe or when the syringe has been filled with more than the desired volume of liquid. In these situations, accidental pushing on the piston rod to return liquid or bubble to the vial will also cause some liquid to be forced through the air channel into the air chamber in the syringe. The way to remove the bubble is a relatively time consuming and complex procedure involving disconnecting the syringe from the vial and reconnecting it. Special attention is required to avoid pushing the plunger accidentally, which slows down the speed of work.

PCT patent application WO2014/122643 to the inventor of the present invention describes improvements to the previously described drug transfer devices that minimize or eliminate the above mentioned limitations. Amongst the improvements taught in WO2014/122643 are embodiments of the drug transfer apparatus that comprises a hydrophobic filter inserted in the air channel in at least one location between the air chamber in the syringe and the fluid transfer component and improved vial adapters.

An inserted filter in the vial adapter serves as barrier between the liquid and air channels, thus preventing the transfer of liquid through the air channel to the air chamber formed at the back of the syringe. Due to insertion of such barrier the user is free to push small air bubbles or correct small over dosage back into the vial during a withdrawal procedure without being concerned that the drug might migrate to the air chamber. On the one hand working with a filter barrier seems to be an advantage but on the other hand the user is motivated to some negligence and it can be expected that users will not clear the filter from liquid before disconnecting the syringe from the vial and some pressure differentials might remain between the air and liquid chambers of the syringe. Therefore right after disconnection the pressure differentials will seek for neutralization and flow of fluids will occur from the chamber with the higher pressure to chamber with the lower pressure until equilibrium is reached. In the case that the lower pressure is in the air chamber, some of the liquid drug will be sucked from the liquid chamber to the air chamber through the path existing between both needle tips inside the double membrane seal actuator. To avoid such migration or transfer due to accidental pushing or pulling the plunger and generally to prevent any uncontrolled migration of liquid to air the chamber, the existing path between the needle tips must be eliminated and total isolation of the needles is required.

Such isolation of the needles constitutes a design challenge. On the one hand, membrane 34b serves as a barrier between the open ends of the needles 38 and 40 and the environment, preventing contaminants such as microorganisms from contaminating the interior of actuator 34 and the needle tips retained in it, thereby maintaining sterility. On the other hand membrane 34b also protects the environment from hazardous substances. While in the previous embodiment in FIG. 1 to FIG. 3b where no filter barrier is used, there is no pressure differential created between the air and liquid chambers, and therefore uncontrolled migration doesn't occur, only accidental pushing or pulling can cause transfer of drug between chambers. Such accidental pushing, which (as a side note) is very common, does not create high pressure inside the double membrane seal actuator since there is free flow from chamber to chamber and high pressure cannot be maintained and collapses immediately until equilibrium is reached. Therefore the sealing properties of the elements in the actuator are never challenged with high pressure and moderate design is sufficient. On the other hand, in embodiments according to WO2014/122643 (see for example FIG. 4) where a filter 50 is inserted as a barrier, there is a requirement for high pressure resistance due to the high pressures of up to 20 atmospheres that can be easily generated by manually pushing the syringe plunger. This phenomenon is especially common with small volume syringes (1-5 ml). Under such pressures most of the isolation designs between the needles will fail and drug will be transferred to the air chamber or even worse, the membranes 34a and 34b cannot resist high pressures, which can cause them to detach from their seat or can cause a leak through the channels in the membranes that were created by the needles during piercing the resilient material of the membrane.

PCT patent application WO2014/181320 and Israeli Patent Application No. 234746, both to the inventor of the present invention, describe needle valves that can be incorporated into the membrane actuator of the connector section 14. The needle valves prevent the possibility of liquid travel through the air conduit from the distal liquid chamber 30 or vial 16 to the proximal air chamber when the connector section 14 is not connected to a vial or other fluid transfer component. The needle valves also simplify the construction of the membrane actuator making it possible to use a single membrane actuator instead of a double membrane actuator as in the connector section shown in FIGS. 1-4.

FIG. 5a and FIG. 6a are schematic cross-sectional views of an apparatus for transferring hazardous drugs. The apparatus and all of the components shown in these figures are identical to those shown in FIG. 1 and FIG. 2a respectively, with two exceptions. The vial adapter 15 comprises a filter 50, as described in WO2014/122643 and the prior art double membrane seal actuator 34 in the connector section 14 comprising two membranes 34a and 34b and arms 35 is replaced with an actuator 52 comprising an embodiment of the needle valve 54, only one membrane 34b, and arms 35. It is important to note that it is not necessary to seal the proximal end of actuator 52 in any fashion because the task of enclosing the ports 56 at the distal ends of the air and liquid conduits when the connector is not connected to another fluid transfer component, which in the prior art was accomplished by membranes 34a and 34b, is accomplished in the single membrane actuator 52 by the needle valve arrangement and membrane 34b alone and in some embodiments by the needle valve itself.

FIG. 5a shows syringe 12 attached to connector section 14 and vial adapter 15 connected to drug vial 16. FIG. 6a shows all components of the apparatus connected together. FIG. 5b and FIG. 6b are enlarged views of the actuator in the apparatus shown in FIG. 5a and FIG. 6a respectively.

Referring to FIG. 5b and FIG. 6b, actuator 52 comprises a needle valve 54 having a valve seat comprising two bores through which the needles of air conduit 38 and liquid conduit 40 pass. It is noted that embodiments of actuator 52 are also described that contain one bore for use in liquid transfer apparatus that comprises only one needle 38.

When the syringe and attached connector are not connected to any other component of the apparatus, as shown in FIG. 5b, the actuator 52 is at the distal end of connector section 14 and the tips of needles 38 and 40 are located in the bores in the seat 54 of the needle valve. In this configuration the ports 56 in the sides of the needles are blocked by the interior walls of the bores completely isolating the needles from each other, thereby preventing air from entering the liquid chamber of the syringe or liquid from entering the air chamber.

When the syringe and attached connector are connected to another component of the apparatus, such as a vial adapter as shown in FIG. 6b, the actuator 52 is pushed towards the proximal end of connector section 14. Since needles 38 and 40 are fixed to the needle holder 36, as actuator 52 moves proximally, the tips of needles 38 and 40 and ports 56 are pushed out through the distal end of the bores in the seat 54 of the needle valve, through membrane 34b, and through membrane 15a of the vial adapter, thereby establishing open fluid paths in the respective channels.

The first goal for the connector is to completely eliminate the possibility of migration of liquid to the air chamber. This can happen, for example, if pressure differentials between the air and liquid chambers exist after disconnection from a vial adapter and if the pressure in the air chamber is lower than that in the liquid chamber, resulting in undesired migration of liquid to the air chamber. The second goal is to prevent leaks or damage to the connector during accidental pushing of the syringe plunger. One of the frequently performed drug transfer operations in hospital settings is known as IV push or bolus injection. Typically the required amount of drug is prepared in a syringe in the hospital pharmacy and delivered to the ward where a qualified nurse administers to the patient the drug through a previously established IV line. A common problem associated with the procedure is that during the trip from pharmacy to ward or at bedside the piston of the syringe is sometimes unintentionally pushed expelling some of the drug from the barrel of the syringe or the piston is unintentionally pulled. High pressures of up to 20 atmospheres can be easily generated by manually pushing the plunger of small volume syringes (1-5 ml). Such pressure may cause the connector to disintegrate or the membranes to be detached. The connector shown in FIG. 5a through FIG. 6b is proposed as a solution to the problems associated with such unintended transfer of fluids between the air and liquid chambers and to resist high pressures created during accidental pushing the of plunger. As can be seen in these figures, when the connector 14 is not connected to the adapter 15, the ports 56 at the distal end of needles 38 and 40 that allow exchange of fluid between the surroundings and the hollow interiors of the needles are blocked by the interior of the bore in seat 54 of the needle valve. If the syringe is filled or partially filled with liquid, then if a force is exerted to try to push the plunger forward and to force liquid to flow through the needle, no liquid can exit the needle through port 56. Conversely, if a force is exerted to pull the plunger backwards no air can enter through port 56 and flow through the interior of the needle into the barrel of the syringe.

Israeli Patent Application No. 237788 to the inventor of the present invention describes embodiments of septum holders for use in syringe connectors that are used to connect syringes to other elements of liquid transfer apparatuses. All of the embodiments of the septum holders described in that patent application comprise a septum holder body, at least one resilient elongated arm that terminates with a distal enlarged element attached to the sides of the body, and a septum. The septum holders of IL237788 are characterized in that they comprise at least one bore that functions as the seat of a needle valve. The bore is created in the septum or in an insert fixed in either the body of the septum holder or in the septum. The septum holders described in IL237788 are also characterized in that the septum is attached to the bottom of the body of the septum holder projecting downwards parallel to the at least one elongated arm.

FIG. 7a, FIG. 7b, and FIG. 7c are respectively front, cross-sectional, and exploded views of an embodiment of a septum holder 58 described in IL237788. Septum holder 58 is comprised of a disk shaped annular body 60. Two equal length resilient elongated arms 62 are attached to the sides of body 60. The arms terminate with distal enlarged elements 64. The bottom part of body 60 is comprised of a cylindrical section that projects downward between arms 62. A cavity 66 is created in the bottom part of body 60 into which is fitted an insert 68 comprising two bores 70 that form the seat of a needle valve. In alternative embodiments insert 68 can have different shapes than that shown and in one embodiment can be comprised of two separate pieces of tubing that are inserted into parallel bores of appropriate diameters created in the bottom part of body 60.

Septum 72 is made of a single piece of cylindrically shaped resilient material. The upper part of septum 72 has a hollow interior forming a cylindrical recess 74 having an inner diameter no larger than that of the outer diameter of the cylindrical section at the bottom of body 60. After insert 68 is fitted into cavity 66, septum 72 is pushed over the bottom part of body 60 until the solid part of septum 72 below recess 74 butts against the bottom of bores 70 in insert 68 thereby isolating the bottoms of the interior of the bores from the external environment. Septum 72 is fixedly held on the body 60 of septum holder 58 by any means known in the art. For example, the resilient material of the septum may be strong enough to grip the sides of the cylindrical section at the bottom of body 60 to hold the septum in place; or, as shown in FIG. 7c, the cylindrical section at the bottom of body 60 may have threads or teeth 76, or an equivalent structure created on its outer surface and septum 72 may have similar structure on the inner diameter of its hollow interior (not shown in FIG. 7c) so that the two structures interlock when septum 72 is pushed over the bottom part of body 60. In other embodiments other methods, such as gluing, ultrasonic forming, or laser or ultrasound welding may be used. The lowest part of septum 72 has a diameter that matches that of the septum in the fluid transfer component, e.g. vial adapter, to which it will be connected.

FIG. 7d schematically shows the holder of FIG. 7a, FIG. 7b, and FIG. 7c in a syringe connector section of a closed system liquid transfer apparatus. The connector section is essentially the same as that in the prior art apparatus described herein above. Cylindrical body 78 of the connector section is attached to syringe 80. Two hollow needles—82, which function as an air conduit, and 84, which functions as a liquid conduit—are fixedly attached to the upper end of body 78 of the connector section. At the lower end of the needles, adjacent to the pointed distal tips, are ports 86 that allow fluid communication between the exterior and the hollow interiors of the needles. External ridges 88 near the bottom of cylindrical body 78 serve as finger grips for use when attaching the connector section and syringe to other elements of the drug transfer system. Ridges 88 are not essential and can be eliminated or replaced with other means, for example a roughened surface area, to accomplish the same purpose.

A septum holder 58 is located inside of cylindrical body 78 of the connector section. As shown, the distal ends of needles 82,84 are inserted into bores 70 in insert 68 (see FIG. 7c). If the insert 68 is made of a flexible material, e.g. silicon, the diameters of bores 70 are smaller than the outer diameter of the shafts of the needles and therefore the resilient material of which the insert is manufactured pushes radially against the shaft of the needle sealing the ports 86. When not connected to another element of a liquid transfer system the distal enlarged elements 64 of arms 62 are engaged in the shoulder portion 90 at the distal end of body 78. As shown in FIG. 7d, in this position the tips of the needles are isolated from the outside by septum 72 at the bottom and the walls of the bores 70 pressing radially on the shafts of the needles prevent fluids from entering or exiting the interior of the needles.

Connection of the syringe connector to a fluid transfer component, e.g. a vial adapter, a spike adapter for connection to an IV bag, or a connector for connection to an IV line, is accomplished in the same manner as in the prior art described herein above. When the septum of the fluid transfer component is pushed against septum 72, septum holder 58 begins to move upwards inside body 78 and the tips of the needles begin to exit bores 70 and penetrate the solid material of septum 72. The tips of the needles pass through septum 72 and the septum of the fluid transfer component as holder 58 continues to be pushed upwards, thereby establishing air and liquid channels between the element of the liquid transfer system attached to the fluid transfer component and the proximal air chamber and distal liquid chamber in the syringe.

It is a purpose of the present invention to provide improved versions of some of the components of the fluid transfer apparatuses of the prior art that will result in simplified manufacturing processes, easier and more efficient use of the components, and safer transfer of liquids.

Further purposes and advantages of this invention will appear as the description proceeds.

SUMMARY OF THE INVENTION

In a first aspect the invention is a septum holder comprising a cylindrically shaped annular body, at least one resilient arm, and a septum that is fixedly attached to the bottom of the body. Each of the at least one arms comprises a distal enlarged element having a rounded outwardly facing rear side and a pointed inwardly facing front side and the enlarged elements at the distal end of the arms move back and forth along lines that are parallel to chords of the circular cross-section of the body of the septum holder.

Embodiments of the septum holder of the invention comprise an insert fitted into the body of the septum holder. The insert has either one or two bores that form the seats of needle valves.

In embodiments of the septum holder of the invention the septum is attached to the outside of the bottom of the body of the septum housing.

In embodiments of the septum holder of the invention comprising two arms that are arranged in pairs, one arm located alongside the other arm on the same side of the septum holder.

In embodiments of the septum holder of the invention the comprising four arms wherein the arms are arranged in two pairs located on opposing sides of the septum holder.

In a second aspect the invention is a connector component comprising a septum holder according to the first aspect of the invention, at least one hollow needle, and an outer housing. The outer housing has the shape of a right prism with a generally square cross-section, an open distal (bottom) end, and a proximal (upper) part adapted to connect to a first component of a fluid transfer system. The outer housing comprises sockets located at the distal end of its inner walls configured to hold the rounded outwardly facing rear side of the distal enlarged element at the bottom of each arm and the inner walls comprise guiding channels to guide the upward or downward movement inside the outer housing of the arms of the septum holder and an adapter component that is attached to the septum holder during a connection or disconnection process between the connector component and the adapter component.

In embodiments of the connector component of the invention the proximal part of the outer housing is manufactured to have one of the following structures: a bore having a straight or tapered interior wall into which a matching cylindrical or conical projection on the first component of the fluid transfer device can be press fitted, glued, or laser or ultrasound welded; a standard male or female Luer type connector; and a Luer connectors that allows uni-directional or bi-directional swiveling of the first component of the fluid transfer device around the vertical symmetry axis of the outer body of the connector.

In embodiments of the connector component of the invention, when the connector component is not connected to any other component of a fluid transfer system, the rounded rear side of distal enlarged elements of the arms are engaged in the sockets at the distal open end of outer housing, the tips of the needles are isolated from the outside at the bottom by the septum and the walls of the bores in the insert in the septum holder press radially on the shafts of the needles thereby preventing fluids from entering or exiting the interior of the needles.

In embodiments of the connector component of the invention each arm and enlarged element has its own set of independent guiding channels and can operate independently from other arms and guiding channels, thereby eliminating deformation of the outer housing or the guiding channels by forces applied by the enlarged elements.

In a third aspect the invention is a swivel-connector comprising a mechanical arrangement structured to allow uni and bi-directional swiveling of a component of a fluid transfer apparatus attached to the swivel-connector. The mechanical arrangement is comprised of:

at least one tooth near the top of the inside wall of the proximal end of a housing of the swivel-connector; a support structure, which comprises a seat for an O-ring and a recess to accommodate the lower end of a Luer element; and at least one tooth created on the top of a horizontal flange near the bottom of the support structure; and a female Luer element with external threads to which a male Luer element can be connected; the bottom of the female Luer element comprising an upper flange and a lower flange with an annular space between them and at least one tooth on the lower surface of the lower flange.

The teeth near the top of the inside wall of a housing of the swivel-connector are configured to hold the female Leur element inside the top of the swivel-connector. The teeth on the support structure of the housing of the swivel-connector have a triangular shape with an upper surface that slopes upwards in a counterclockwise direction and ends at a vertical back surface and the teeth on the bottom of the lower flange of the female Luer element have an upper surface that slopes upwards in a clockwise direction and ends at a vertical back surface. The teeth are located and oriented on their respective flanges such that if the Luer element is turned relative to the swivel-connector housing in the counterclockwise direction, then the sloping surfaces of the teeth on both flanges will slide over each other allowing the rotation to be carried out in this direction and if the Luer element is turned relative to the swivel-connector housing in the clockwise direction, then the vertical surfaces on the teeth on both flanges will butt up against each other preventing relative motion between the female Luer element and swivel-connector housing in this direction.

Embodiments of the swivel-connector of the invention comprise a space between the bottom of the teeth near the top of the inside wall of the proximal end of a housing of the swivel-connector and the top of the upper flange of the female Luer element. This allows the Luer element to be lifted the height of this space, whereupon the teeth on the on the support structure of the housing are vertically separated from the teeth the teeth on the bottom of the lower flange of the female Luer element so that they can't interact with each other. This allows the female Luer element to be rotated clockwise relative to the swivel-connector housing.

In a fourth aspect the invention is a factory assembled syringe-connector unit, which comprises:

a syringe comprising a throat at the bottom of the syringe that comprises an upper and a lower flange with an annular space between them; and a connector having a housing comprising at least one tooth projecting inwards from near the top of the inner wall of the proximal of the housing.

The distal end of the syringe and the proximal end of the connector are manufactured from plastic that will flex when they are pushed together with sufficient force, thereby allowing the lower flange to pass the at least one tooth until the at least one tooth is located in the annular space holding the syringe and the connector together. In this configuration the syringe and connector can be swiveled relative to each other in either clockwise or counterclockwise directions around their common longitudinal symmetry axis.

In a fifth aspect the invention is an adapter component for connection between a connector component according to the second aspect of the invention that comprises a septum holder according to the first aspect of the invention and a second component of a fluid transfer device. The adapter component comprises an elongated extension having an external surface comprising features structured to couple with the septum holder.

In embodiments of the adapter component of the invention in which the septum holder comprises two arms the features structured to couple with the septum holder comprise for each of the two arms: a vertical groove and a cut-out portion adapted to allow room for the arm and enlarged element at the distal end of the arm to move during the connection/disconnection process and a step-like structure located near the top of the elongated extension.

The step-like structure comprises: a first planar vertical surface on a side of the step-like structure facing away from the vertical groove configured to slide along a guiding channel in the connector component; a second planar vertical surface on a side of the step-like structure facing towards the vertical groove configured to slide along the tip of the pointed inwardly facing front side of the enlarged element at the distal end of the arm; and a planar horizontal bottom surface configured to engage the top surface of the pointed inwardly facing front side of the enlarged element at the distal end of the arm.

In embodiments of the adapter component of the invention in which the septum holder comprises four arms the features structured to couple with the septum holder comprise for each pair consisting of two arms a house-shaped structure located near the top of the elongated extension.

The house-shaped structure comprising two planar vertical surfaces configured to slide along the tips of the pointed inwardly facing front side of the enlarged element at the distal ends of the two arms in the pair and a planar horizontal bottom surface configured to engage the top surfaces of the pointed inwardly facing front sides of the enlarged elements at the distal ends of the two arms in the pair.

Embodiments of the adapter component of the invention are configured to connect to one of: a vial, an IV bag, and an IV line.

In a sixth aspect the invention is a syringe comprising a sealing element at its proximal end. The sealing element comprises a disk shaped annular sealing assembly having a hole in its center through which piston rod passes and an O-ring that seals around the piston rod. The syringe is characterized in that the sealing element is located inside its barrel.

In embodiments of the syringe of the invention the sealing assembly is held in place and sealed to the inside of the syringe barrel by at least one of: press fitting into the barrel, laser or ultrasound welding, heat welding, and gluing.

All the above and other characteristics and advantages of the invention will be further understood through the following illustrative and non-limitative description of embodiments thereof, with reference to the appended drawings.

BRIEF DESCRIPTION OF THE DRAWINGS

FIG. 1 is a schematic cross-sectional view of a prior art apparatus for transferring hazardous drugs;

FIG. 2a to FIG. 2d are cross-sectional views that schematically show the 4 steps connection sequence between the connector section and the vial adapter of the apparatus of FIG. 1;

FIG. 3a and FIG. 3b are cross-sectional views that schematically show the concept of using the apparatus of FIG. 1 for transferring hazardous drugs;

FIG. 4 shows an embodiment of the apparatus of FIG. 1 in which a filter is introduced into the air channel by placing it in the vial adapter;

FIG. 5a and FIG. 6a are schematic cross-sectional views of a prior art apparatus for transferring hazardous drugs identical to that shown in FIG. 4 disconnected from and connected to a vial adapter respectively, with the exception that the prior art double membrane seal actuator is replaced with an actuator comprising a single membrane and an embodiment of a needle valve;

FIG. 5b and FIG. 6b are enlarged views of the actuator in the apparatus shown in FIG. 5a and FIG. 6a respectively;

FIG. 7a, FIG. 7b, and FIG. 7c are respectively front, cross-sectional, and exploded views of a first embodiment of a prior art septum holder;

FIG. 7d schematically shows the holder of FIG. 7a in a connector section of a closed system drug transfer apparatus;

FIG. 8a schematically shows a fluid transfer apparatus in which is incorporated the improved components of the present invention;

FIG. 8b symbolically shows all components of the fluid transfer apparatus of FIG. 8a connected together;

FIG. 9a and FIG. 9b schematically show embodiments of a septum holder of the present invention;

FIG. 10a and FIG. 10b schematically show the difference between the attachment of the arms to the septum holder of the prior art and the septum holder of the present invention;

FIG. 11a symbolically shows an adapter component for connection to a septum holder having two arms according to the present invention;

FIG. 11b schematically shows the adapter component of FIG. 11a connected to a septum holder;

FIG. 12a symbolically shows an adapter for connection to a septum holder having four arms according to the present invention;

FIG. 12b schematically shows the adapter of FIG. 12a connected to a septum holder;

FIG. 13 shows an adapter for connecting a septum holder of a connector component according to the present invention to a spike port of an IV bag;

FIG. 14 schematically shows the exterior of a connector component according to the present invention;

FIG. 15a to FIG. 15d symbolically show different stages in the connection of a connector component to an adapter component according to the invention;

FIG. 16a to FIG. 19 schematically show an embodiment of the proximal end of a connector that comprises a mechanical arrangement that allows bi-directional swiveling of a component of a fluid transfer apparatus attached to the adapter;

FIG. 20a and FIG. 20b schematically show an embodiment of the proximal end of a connector that allows bi-directional swiveling of a syringe that is factory attached to it;

FIG. 21a schematically shows the proximal end of a prior art syringe; and

FIG. 21b to FIG. 21d schematically show the proximal end of an embodiment of a syringe according to the invention.

DETAILED DESCRIPTION OF EMBODIMENTS OF THE INVENTION

The present invention is improved versions of some of the components of the fluid transfer apparatuses described in the background section of this application. FIG. 8a schematically shows fluid transfer apparatus 100 in which are incorporated the improvements of the present invention.

Apparatus 100 comprises a first component—in this case syringe 102, a connector component 104, an adapter component 106 to allow connection of connector component 104 to a second component—in this case vial 108.

The changes that have been made to apparatus 100 relative to the prior art and which will be described in detail below are the following:

the elements that seal the proximal end of the syringe 102 have been redesigned resulting in an improved syringe;

the arms on the septum holder in the connector component 104 have been redesigned and the way in which they move in order to carry out their function has been changed;

the exterior and interior of the outer housing of the connector component 104 have been redesigned in view of the changes in the arms on the septum housing;

the end of connector component 104 that connects to the first drug container comprises a swivel function in some embodiments; and the proximal end of adapter component 106 has been changed to allow it to be connected to connector component 104.

FIG. 8b symbolically shows the first and second components 102,108 of fluid transfer apparatus 100 connected together by means of connector component 104 and adapter component 106.

FIG. 9a and FIG. 9b schematically show embodiments of septum holder 110 of the present invention. The septum holders shown in these figures are identical with the exception of the number of resilient arms 118—two arms in FIG. 9a and four arms in FIG. 9b.

Septum holder 110 is comprised of a cylindrically shaped annular body 112. Two (or four) parallel equal length, downward extending, resilient, elongated arms 118 are attached to the sides of body 112. The arms terminate with distal enlarged elements 120. The distal enlarged elements are shaped roughly like a human foot with a rounded outwardly facing rear side and a pointed inwardly facing front side. The bottom section of body 112 is comprised of a cylindrical section that projects downward parallel to arms 118. A cavity is created in the bottom part of body 112 into which is fitted an insert comprising one or two bores that form the seats of needle valves. Ribs 114 or equivalent structure may be present in the interior of body 112 to provide mechanical strength and support to the insert.

Septum 116 is made of a single piece of cylindrically shaped resilient material. The upper part of septum 116 has a hollow interior forming a cylindrical recess having an inner diameter no larger than that of the outer diameter of the cylindrical section at the bottom of body 112. After the insert is fitted into the cavity in body 112, septum 118 is fitted over the cylindrical bottom section of body 112 (much as a knitted cap is pulled over a head) until the solid part of septum 118 butts against the bottom of the bores in the insert; thereby isolating the bottoms of the interior of the bores from the external environment. Septum 118 is fixedly held facing downward on the body 112 of septum holder 110 by any means known in the art, such as described herein above.

FIG. 10a and FIG. 10b schematically show the difference between the attachment of the arms to the septum holder of the prior art and the septum holder of the present invention. In the prior art a pair of arms is located facing each other on opposite sides of the septum holder. The enlarged elements at the distal end of the arms move back and forth along an extension of a diameter of the circular cross-section of the body of the septum holder in the direction shown by the double headed arrows in FIG. 10a. In the septum holder of the invention a pair of arms is located one alongside the other on the same side of the septum holder. The enlarged elements at the distal end of the arms move back and forth along extensions of parallel chords of the circular cross-section of the body of the septum holder in the directions shown by the double headed arrows in FIG. 10b.

With the exception of the location at which the arms 118 are attached to the sides of body 112, septum holder 110 is essentially identical to the prior art septum holder 58 described herein above in relation to FIG. 7a to FIG. 7c For this reason most of the structural elements of septum holder 110 are not illustrated herein and the reader is directed to FIG. 7a, FIG. 7b, and FIG. 7c to see the corresponding structure in the prior art. It is noted that other prior art septum housings, for example the other embodiments described in the above referenced IL 23788, can be adapted mutatis mutandis, by locating the arms as described with reference to FIGS. 9a and 9b. It is also noted that septum housings according to this invention can be manufactured having only one arm or more than four arms. A very stable configuration can be obtained by the use of three arms, although this would be a more complex embodiment to manufacture.

FIG. 11a symbolically shows an adapter component 106 for connection to a septum holder 110 having two arms according to the present invention. The distal (lower portion) of adapter component 106 is adapted to connect to the second component of the fluid transfer apparatus and is not relevant to the present invention. As in the prior art the interior of the hollow elongated extension 122 of adapter component 106 contains a channel or channels to allow fluid communication between the interior of the second component of the fluid transfer system and the needles in the connector component 104, when connector component 104 and adapter component 106 are connected. A septum 124 at the top of the elongated extension seals the interior channels when adapter component 124 is not connected to another element of a fluid transfer apparatus.

The exterior of elongated extension 122 is significantly different from that of prior art adapter elements (see for example FIG. 5b). On the exterior surface are created—for each of the two arms, a vertical groove 130, a cut-out portion 128, and a step-like structure 126a. The functional parts of section 126a are planar vertical surface 126b, planar vertical surface 126c, and planar horizontal bottom surface 126d. The functions of these parts of 126a will be described in more detail herein below.

FIG. 11b schematically shows the elongated extension 122 of the adapter component of FIG. 11a connected to septum holder 110. Elongated extension 122 comprises groove 130 and cut-out portion 128 in which the enlarged element 120 at the distal end of arm 118 can move. If the diameter of the elongated extension 122 is small enough, then groove 130 is not necessary. When the connection is complete, the flat upper surface of the pointed front side of enlarged element 120 is caught under the flat lower surface 126d of 126b locking the septum holder 110 and adapter 106 together.

FIG. 12a symbolically shows an adapter component 106 for connection to a septum holder 110 having four arms according to the present invention. In this case there is created a projecting "house-shaped" structure inside a cut-out portion 134 on opposite sides of the outer surface of the proximal end of the elongated extension 122.

FIG. 12b schematically shows the adapter component of FIG. 12a connected to a septum holder 110. The enlarged elements 120 at the distal ends of arms 118 fit into the cut-out portion 134. The flat upper surface of the "toes" of enlarged elements 120 are caught under the flat lower surface of "house" 132 locking the septum holder 110 and adapter component 106 together.

The changes to the exterior surface of the elongated extension of the adapter component dictated by the present invention can be made mutatis mutandis to any of the adapters described in the prior art discussed in the background section of this application, e.g. a vial adapter, a spike adapter for connection to an IV bag, or a connector for connection to an IV line. FIG. 13 shows an adapter component 136 for connecting a to a spike port of an IV bag. Adapter component 136 has an elongated extension 138 whose upper part has the same structure as shown in FIG. 11a; thereby allowing a septum holder such as shown in FIG. 9b to be attached to adapter component 136.

FIG. 14 schematically shows the exterior of connector component 104. The internal elements of connector 104, i.e. the septum holder and one or two needles, are surrounded by an outer housing 140. Outer housing 140 has the shape of a right prism with a generally square cross-section and an open distal (bottom) end into which the proximal end of elongated extension 122 of adapter component 106 can be inserted. The proximal (upper) part 142 of outer housing 140 can be constructed in many ways in order to connect to a first component, e.g. a syringe or an IV line, of a fluid transfer apparatus. Some of the ways in which proximal part 142 can be constructed include: a bore having a straight or tapered interior wall into which a matching cylindrical or conical projection on the component of the fluid transfer device can be press fitted, glued, or laser or ultrasound welded; standard male or female Luer type connectors; or newly designed Luer connectors that allow unidirectional or bi-directional swiveling of the component of the fluid transfer device around the vertical symmetry axis of the outer housing 140 of the connector 104. The swivel type connectors will be described herein below with reference to FIGS. 16a-20a.

FIG. 15a to FIG. 15d symbolically show different stages in the connection of a connector component 104 of the invention to an adapter component 106 of the invention. As in the prior art apparatuses of the applicant, the connection is done by pushing the two components together and the "steps" of the process are similar. Also, as in the prior art, although the process is illustrated as a series of steps, in actual practice it is carried out with one continuous smooth action. In these figures, the connector component has been rotated and part of outer housing 140 has been removed to allow one arm 118 of septum holder 110 to be seen. The one or two needles are not shown.

In FIG. 15a the proximal end of elongated extension 122 of adapter component 106 has been inserted into the open distal end of outer housing 140. Septum 116 of the connector component has not yet contacted septum 124 of the adapter section and the arm 120 is in its normal relaxed configuration with the rounded rear side of the enlarged element 120 in a socket 146 that is created at the distal end of outer housing 140 (see FIG. 15d). The socket 146 is part of a guiding channel 113 that is formed as a cavity in the interior surface or as a rib extending from the interior surface of the plastic outer housing 140. Guiding channel 113 guides and positions the rounded rear side of the enlarged element 120 according the respective operation steps. Another corresponding guiding channel 111, which is made in a similar manner to channel 113, guides the planar vertical surface 126b, which glides along it.

In embodiments not illustrated herein, the sockets 146 and guiding channels 111 and 113 are not formed on the interior wall of the outer housing but are constructed in a frame-like structure that is supported within the outer housing.

In FIG. 15b the two septa 116 and 124 are in the middle of the process of being pressed against each other, but the septum holder 110 has not started to move upwards inside outer housing 140 because the enlarged element 120 remains immovably trapped inside of socket 146 with its rounded rear side inside of socket 146 and the tip of its pointed front side pressed against the vertical surface 126c of element 126a on the adapter component. Enlarged element 120 will remain trapped until the septa are fully pressed together and only then it will be released for movement. Although the enlarged element 120 is pressing on the vertical surface 126c, the vertical surface 126c which is part of element 126a is prevented from moving sidewards because the planar vertical surface 126b is pressed against guiding channel 111. The vertical surface 126b of the elongated extension 122 of adapter component 106 glides along the channel 111 inside outer housing 140 and thereby dictates straight axial motion of the components during the connection (and disconnection) process.

In FIG. 15c elongated extension 122 of adapter component 106 has advanced far enough into the interior of connector component 104 that the force used to press the two septa against each other forces septa holder 110 to start moving upward. The upper surface of the rounded rear side of enlarged element 120 slides along a sloped upper surface of socket 146 pushing the pointed front side of enlarged element 120 against vertical surface 126c of element 126a on the adapter component. As more force is applied the septa are pushed closer together and elongated extension 122 moves up relative to septum housing far enough so that the pointed front side of enlarged element 120 at the end of arm 118 passes the bottom of vertical surface 126c.

In FIG. 15d the upper part of the pointed front side of enlarged element 120 is hooked under the horizontal bottom surface 126d of element 126a on the elongated extension 122 of adapter component 106. The septum holder 110 and adapter component 106 continue to move up inside outer housing 140 of connector section coupled together. Also seen in FIG. 15d are ribs 144 that are formed on the inside of the outer housing 140 to provide mechanical strength.

As described with reference to the prior art fluid transfer apparatuses of the applicant, when the connector component 104 is not connected to any other component of a fluid transfer system, the rounded rear side of distal enlarged elements 120 of arms 118 are engaged in the sockets 146 at the distal open end of outer housing 142. In this position the tips of the needles are isolated from the outside at the bottom by septum 116 and the walls of the bores in the insert pressing radially on the shafts of the needles prevent fluids from entering or exiting the interior of the needles.

As described with reference to the prior art fluid transfer apparatuses of the applicant, when the connected septum holder 110 and adapter component 106 move upwards the needle or needles in the connector component penetrate the two septa 116 and 124 establishing a pathway for fluid communication between components of the fluid transfer system that are connected respectively to the proximal end of the connector component 104 and the distal end of adapter component 106.

The embodiment of the septum holder shown in FIG. 12a and FIG. 12b has four arms 120, which are actually two pairs of arms. This embodiment provides a balance of forces in comparison to the embodiment of septum holder shown in FIG. 15a to FIG. 15d that comprises two arms only. During all steps of the connection operation each of the arms 120 in a pair of arms in FIG. 12a and FIG. 12b presses on one side of the flat side surface of "house" 132 and tries to rotate it sideward. But since there are pairs of arms that work in opposing directions, the force that is applied by one arm is neutralized by the force applied by the other arm of the pair. The balanced pair of arms pressing one against the other eliminates the need for an equivalent component to gliding channel 111 inside the outer housing 140 and the planar vertical surface 126b as shown in FIG. 15a to FIG. 15d.

One of the main reasons for developing the connector component 104 described herein above is that in the prior art connector the arms and the enlarged elements at their distal ends exert great force on the inner walls of the connector body during operation. As a result the connector body, which is made of plastic, tends to deform by increasing its diameter. This may cause malfunction of the connector and breach of safety. One such typical malfunction is caused during disconnection: in normal operation during the disconnection procedure the connector and the adapter are pulled apart; during pulling the adapter port is held by the enlarged elements and only when they reach the area at the distal end of the connector body that has larger diameter (distal shoulder portion 19 in FIG. 1) are they able to expand and to release the adapter that they have been holding all that time and the disconnection is complete. The problem occurs when the body is deformed due to the side forces that the enlarged elements are applying on the inner walls of the connector body. This deformation simulates the distal shoulder portion and the enlarged elements release the adapter too early, i.e. before the enlarged elements reach their destination in the distal shoulder portion and remain in a position that is a little too deep inside the connector after the adapter has been released. The disconnection seems at first glance to be properly executed, but the reality is that since the enlarged elements were left too deep inside the connector body, when another connection is to be made the adapter will not slide between the enlarged elements and be held by them. In the contrary, the enlarged elements will be pushed by the adapter inside the body without creating any connection and the needles will pierce the membranes and appear exposed to the environment and possibly leak while breaking the closed system.

An advantage of the new connector component 104 is that it doesn't rely on the stability of the connector body, since the arms and enlarged elements slide in the channels 111 and 113 formed by the rigid ribs that are formed on the inside of the outer housing 140. Unlike the prior art each arm and enlarged element has its own set of independent guiding channels and can operate independently from other arms and guiding channels and the forces that the enlarged elements apply don't deform the outer housing or the guiding channels.

Another advantage of the new connector component is that the design allows for construction of a smaller connector and respective adapter since, amongst other factors there is no need for the bulky distal shoulder portion of the prior art connector. Size is a crucial factor with users since smaller products are easier to handle and will be preferred in most applications.

FIG. 16a to FIG. 19 schematically show an embodiment of the proximal end of a connector that comprises a mechanical arrangement that allows uni and bi-directional swiveling of a component of a fluid transfer apparatus attached to the connector. A special female Luer lock is provided on the proximal end of the connector and any device such as infusion tubing or a syringe with male Luer lock can be attached to it by a clockwise twisting motion. During the down pressing and clockwise twisting motion of the male Luer lock, rotation of the female Luer element of the connector is prevented as will be described herein below, thereby allowing the male Luer element to be rotated until the connection is tight and no further twisting is necessary or possible. After the connection of the two Luer elements is completed, any attempt to twist them counterclockwise will result in endless swiveling without any disconnection occurring. The purpose of this arrangement is to prevent both, the unintended and the intended disconnection by the users, such as by children in hospital while playing with an infusion tubing connection. Further, if the male Luer element is lifted a little and rotated clockwise, this will also result in an endless swiveling. All parts that could be used for gripping to unlock the connection are inaccessible in this embodiment thereby providing a tamper proof Luer lock connection. This arrangement can be used with all embodiments of both the prior art connectors described in the background section of this application and the new connector components described herein.

FIG. 16a shows a connector component 104 of the present invention adapted as a swivel connector. Proximal end 142 of outer housing 140 is a specially designed female Luer element 148 with external threads 150 to which a male Luer element can be connected. FIG. 16b is a cross-sectional view of FIG. 16a. Seen in FIG. 16b are teeth 152 on the inner wall of proximal end 142 that hold Luer element 148 inside of connector component 104 and the channels 113 in which the arms 118 of the septum holder 110 move as the septum holder moves up and down inside the connector element. Also seen are needle holder 168 that attaches the proximal end of needle 166 to the outer housing of the connector component. As can be seen and has been described herein above, when the connector component is not connected to an adapter component, the tip of needle 166 is located inside of the insert in the body of the septum holder.

FIG. 17a shows a prior art connector 14 modified to have a proximal end 142 according to the present invention. Area A, in which a section of the wall of proximal end is removed to show the internal elements, is enlarged in FIG. 19.

FIG. 17b is an exploded view showing the main parts of which the swivel connector is assembled and how the bottom of the Luer element is designed. The swivel connector is comprised of a connector 14 (or 104) as described herein above, whose upper end has been modified, the female Luer element 148, and an O-ring, which prevents leakage of fluid between the connector body and Luer element in the assembled swivel connector. The bottom of Luer element 148 comprises an upper flange 162 and a lower flange 154 with an annular space 160 between them. Flange 154 has one or more (typically four) teeth 156 on its lower surface that are part of the swivel mechanism.

Referring now to FIG. 18, which is a cross-sectional view of the proximal end 142 of the connector housing. The modifications made to this part of the connector include the creation of one or more (typically four) teeth 152 near the top of the inside wall; a support structure 157, which comprises a seat for O-ring 164 and a recess to accommodate the lower end of Luer element 148; and one or more (typically four) teeth 158 created on a horizontal flange near the bottom of support structure 157.

To assemble the swivel connector O-ring 164 is placed in its seat and then Luer element 148 is pushed into the recess in the proximal end 140 of the connector housing. All parts of the Luer element and the connector housing are made of plastic that has enough resilience that flange 154 on the bottom of the Luer element can be forced past teeth 152, which move into space 160 holding the Luer element and housing of the connector together.

Referring now to FIG. 19 it can be seen that teeth 158 on the support structure 157 of the housing of the connector have a triangular shape with an upper surface that slopes upwards in a counterclockwise direction and ends at a vertical back surface and the teeth 156 on the bottom of flange 154 have an upper surface that slopes upwards in a clockwise direction and ends at a vertical back surface. If it is attempted to swivel Luer element 148 relative to the connector housing in the counterclockwise direction, then the sloping surfaces of teeth 154 and 156 will slide over each other and Luer element 148 will rise relative to the connector housing until these surfaces pass each other and then the Luer element will drop down and can continue to turn until the next pair of teeth encounter each other when the process repeats. On the other hand, if it is attempted to swivel Luer element 148 in the clockwise direction, then the vertical surfaces on teeth 154 and 156 will butt up against each other preventing relative motion between the Luer element and connector housing in this direction.

The distance "h" between the bottom of teeth 152 and the top of flange 154 allows the Luer element 148 to be lifted the height of "h" and swiveled clockwise; because, when the Luer element 148 is lifted to height "h" the teeth 152 and 158 are separated from each other so they can't interact with each other. When the Luer element is pressed downward and the distance "h" between the teeth 152 and 158 is eliminated, the teeth will engage each other and rotation clockwise will tighten even more the connection between the male and female Luer elements until it is not possible to twist anymore. This uni and bi-directional swivel feature prevents unintended disconnection of tubing or a syringe that has been Luer-locked to a connector, which is a not uncommon problem that occurs in the prior art. In order to separate the two Luer-locked components they must be turned counterclockwise to each other. With the swivel connector of the invention one component will freely spin with relation to the other and they will not disconnect.

FIG. 20a and FIG. 20b schematically show an embodiment of the proximal end of a connector that allows bi-directional swiveling of a syringe that is attached to it. This syringe-connector unit is factory assembled and can comprise all embodiments of both the prior art connectors described in the background section of this application and the new connector components described herein.

FIG. 20a is an exploded view showing the components of the syringe-connector assembly. The throat at the bottom of the syringe is manufactured so that it comprises two flanges 170 and 172 with an annular space 174 between them. The proximal end 142 of the housing 14 (or 140) of the connector is manufactured with at least one tooth projecting inwards from near the top of the inner wall of the proximal end 142 of its housing.

FIG. 20b is a cross-sectional view showing the factory assembled syringe-connector unit. After the O-ring 164 is placed in its seat, the distal end of the syringe 12 and the proximal end 142 of the connector are pushed together with sufficient force to allow the plastic parts to flex enough so that flange 170 passes teeth 152 and the teeth are located in annular space 174 holding syringe 12 and connector 14 together. The O-ring prevents leakage of fluid between the connector body and syringe and the syringe is now able to swivel freely in both clockwise and counterclockwise directions relative to the connector.

This swivel feature in the factory assembled syringe with connector is an improvement in comparison to prior art's stiff welded syringe with connector. One advantage is that when a Luer-lock-adapter (a component of a drug transfer system) is screwed on an infusion tubing and a prior art syringe with connector is connected to the adapter, it could happen that the user will unscrew the adapter by rotating the attached syringe. This can happen because hospital personnel are used to screw or unscrew (Luer-lock or un-Luer) most of the equipment in the hospital. It can also happen when the user, e.g. pharmacist or nurse, twists the syringe in order to read the measurement marks. With the swivel design the syringe will spin in relation to the connector, unscrewing will be prevented and the user, can easily and safely rotate the syringe to have an unobstructed view of the measurement markings on it.

FIG. 21a schematically shows the proximal end of a prior art syringe. In this syringe, in order to seal the distal end, a lid 180 is snapped over the flange 176 that forms the finger grip at the top of the syringe barrel 18. An O-ring around piston shaft 24 and a gasket 182 isolate the interior of the syringe from the outside.

This solution for sealing the top of the syringe, whether for closed or open systems, means that the lid adds to the thickness of the flange that exists on the syringe barrel. Such additional thickness hinders insertion of the syringe into most of the existing electronic syringe pumps that are used in hospitals for precise administration. Such pumps have dedicated grooves for the syringe shape and are designed to accommodate standard syringes.

The solution proposed by the present invention is to replace external lid 180 with a sealing element that is positioned inside the barrel of an existing syringe. FIG. 21b to FIG. 21d schematically show the proximal end of an embodiment of a method of sealing the distal end of the syringe according to the invention. This sealing element comprises a disk shaped annular sealing assembly 184 having a hole in its center through which piston rod 24 passes. This embodiment is comprised of an upper part 184a and a lower part 184b that are pressed together to hold an O-ring that seals around the piston rod. The sealing assembly is pushed into the top of the barrel of the syringe as shown in FIG. 21c and FIG. 21d. The sealing assembly 184 is then held in place and sealed to the inside of the syringe barrel by laser or ultrasound welding, heat welding or gluing at the location indicated by the arrows in FIG. 21c. Alternatively the sealing assembly 184 can be press fitted into the barrel and held in place by friction and the lateral forces exerted by the sides of the plastic barrel and the sealing assembly against each other. For added strength a notch 186 in the sealing assembly can snap into a ridge 188 on the inside wall of the syringe barrel.

Embodiments of standard syringes that are not used in closed transfer systems can have a design that is not airtight, e.g. they can be provided with ventilation holes that are either open directly to the surroundings or protected by filters.

The sealing assembly 184 provides a solution to the prior art problem because it is placed inside the barrel and doesn't disturb the external shape of the syringe. Therefore it is compatible with syringe pumps and other medical equipment. Furthermore, it is easier to manufacture and in airtight applications it saves a whole component and its assembly, namely, the insertion of sealing ring between the lid and the barrel, which is difficult to accomplish correctly, is eliminated.

Although embodiments of the invention have been described by way of illustration, it will be understood that the invention may be carried out with many variations, modifications, and adaptations, without exceeding the scope of the claims.

The invention claimed is:

1. A system comprised of a syringe and a connector configured to be joined together such that the syringe and the connector can be swiveled relative to each other around a common longitudinal axis, wherein the connector comprises a mechanical arrangement structured to join the syringe and the connector and to allow uni- and bi-directional swiveling of the syringe and the connector relative to each other, the mechanical arrangement comprising:

at least one tooth near a top of an inside wall of a proximal end of a housing of the connector; a support structure, which comprises a seat for an O-ring and a recess to accommodate a lower end of a Luer element; and at least one tooth created on a top of a horizontal flange near a bottom of the support structure; and a female Luer element with external threads to which a male Luer element at a tip of the syringe is connected; a bottom of the female Luer element comprising an upper flange and a lower flange with an annular space therebetween and at least one tooth on a lower surface of the lower flange;

wherein, the at least one tooth near the top of the inside wall of the housing of the connector is configured to hold the female Luer element inside the top of the connector;

wherein, the at least one tooth on the support structure of the housing of the connector has a triangular shape with an upper surface that slopes upwards in a counterclockwise direction and ends at a vertical back surface and the at least one tooth on the lower flange of the female Luer element has an upper surface that slopes upwards in a clockwise direction and ends at a vertical back surface;

wherein the at least one tooth on the support structure and the at least one tooth on the female Luer element are located and oriented on their respective flanges such that if the female Luer element and the syringe are turned relative to the connector housing in the counterclockwise direction, then the sloping surfaces of the at least one tooth on the support structure and the at least one tooth on the female Luer element slide over each other allowing the rotation to be carried out in this direction and if the female Luer element and the syringe are turned relative to the connector housing in the clockwise direction, then the vertical surfaces on the at least one tooth on the support structure and the at least one tooth on the female Luer element butt up against each other preventing relative motion between the female Luer element and the housing of the connector in this direction;

wherein, the connector comprises a space between a bottom of the at least one tooth near the top of the inside wall of the proximal end of the housing of the connector and a top of the upper flange of the female Luer element, which allows the female Luer element to be lifted a height of this space, whereupon the at least one tooth on the support structure of the housing are vertically separated from the at least one tooth on the lower flange of the female Luer element so that the at least one tooth on the support structure and the at least one tooth on the female Luer element can't interact with each other, thereby allowing the female Luer element and the syringe to be rotated clockwise relative to the housing of the connector.

2. The system of claim 1 wherein the syringe and the connector are configured to form a factory assembled unit; wherein:

the syringe comprises a throat at a bottom of the syringe that comprises an upper and a lower flange with an annular space therebetween; and the housing of the connector has at least one tooth projecting inwards from near the top of the inside wall of the proximal end of the housing;

wherein, a distal end of the syringe and the proximal end of the housing are manufactured from plastic that will flex when the syringe and the housing are pushed together with a predetermined force, thereby allowing the lower flange of the throat to pass the at least one tooth projecting inwards from the inside wall of the housing until the at least one tooth projecting inwards from the inner wall of the housing is located in the annular space; thereby holding the syringe and the connector together, thereby allowing the syringe and connector to be swiveled relative to each other in either clockwise or counterclockwise directions around the common longitudinal symmetry axis.

* * * * *